US005885996A

United States Patent [19]
Webber et al.

[11] Patent Number: 5,885,996
[45] Date of Patent: Mar. 23, 1999

[54] ANTIPROLIFERATIVE QUINAZOLINES

[75] Inventors: Stephen E. Webber, San Diego; Ted M. Bleckman, La Jolla; John Attard; Terrence R. Jones, both of San Diego; Michael D. Varney, Carlsbad, all of Calif.

[73] Assignee: Agouron Pharmaceuticals, Inc., La Jolla, Calif.

[21] Appl. No.: 923,117

[22] Filed: Sep. 4, 1997

Related U.S. Application Data

[62] Division of Ser. No. 418,415, Apr. 7, 1995, Pat. No. 5,707,992, which is a continuation of Ser. No. 861,030, Mar. 31, 1992, Pat. No. 5,430,148.

[51] Int. Cl.$^6$ .................. A61K 31/505; A61K 31/54; C07D 239/90; C07D 403/02
[52] U.S. Cl. .................. 514/253; 514/259; 514/260; 514/898; 514/895; 514/896; 544/238; 544/284; 544/285; 544/287; 544/289
[58] Field of Search .................. 544/284, 238, 544/285, 287, 289; 514/253, 259, 260, 898, 895, 896

[56] References Cited

U.S. PATENT DOCUMENTS

| | | | |
|---|---|---|---|
| 1,817,982 | 8/1931 | Hentrich et al. | 514/259 |
| 3,542,779 | 11/1970 | Ecersy et al. | 514/259 |
| 3,546,224 | 12/1970 | Davoll | 514/259 |
| 4,048,312 | 9/1977 | Lacefield | 514/259 |
| 4,223,143 | 9/1980 | Cuny | 514/259 |
| 4,251,531 | 2/1981 | Dorie et al. | 514/259 |
| 4,391,809 | 7/1983 | Elslager | 514/259 |
| 4,564,616 | 1/1986 | Jones et al. | 514/260 |
| 4,668,682 | 5/1987 | Sekiya et al. | 514/259 |
| 4,749,698 | 6/1988 | Neiss et al. | 514/259 |
| 4,853,221 | 8/1989 | Elslager et al. | 514/259 |
| 4,857,530 | 8/1989 | Berman et al. | 514/260 |
| 4,981,856 | 1/1991 | Hughes | 514/260 |
| 4,985,441 | 1/1991 | Hughes et al. | 514/260 |
| 5,089,499 | 2/1992 | Barker et al. | 514/259 |
| 5,430,148 | 7/1995 | Webber et al. | 544/238 |
| 5,707,992 | 1/1998 | Webber et al. | 514/253 |

FOREIGN PATENT DOCUMENTS

| | | |
|---|---|---|
| 793845 | 9/1968 | Canada . |
| 365763 | 5/1990 | European Pat. Off. . |
| 373891 | 6/1990 | European Pat. Off. . |
| 459730 | 12/1991 | European Pat. Off. . |
| 57-156467 | 9/1982 | Japan . |
| 1045180 | 10/1966 | United Kingdom . |
| 1078887 | 8/1967 | United Kingdom . |
| 206565 | 7/1981 | United Kingdom . |
| 2065653 | 7/1981 | United Kingdom . |
| 2175903 | 12/1986 | United Kingdom . |

OTHER PUBLICATIONS

Ashton, et al., "Synthesis of 5–Substituted Quinazolines as Potential Antimalarial Agents," *Journal of Medicinal Chemistry*, vol. 16, 1233–1237 (1973).

Marvel, C.S., et al., "Isatin," *Organic Synthesis*, 327–330.

Krowicki, "4–Mercapto–2(1H)–pyridinethione," *Polish Journal of Chemistry*, vol. 53, 701–707 (1979).

Ghose et al., "General Distance Geometry Three–Dimensional Receptor Model for Diverse Dihydrofolate Reductase Inhibitors," *Journal of Medicinal Chemistry*, vol. 27 (1984), pp. 901–914.

Fukunaga et al., "Inhibition of Dihydrofolate Reductase. Structure–Activity Correlations of Quinazolines," *Journal of Medicinal Chemistry*, vol. 19 (1976), pp. 605–611.

Jones et al., "A Potent Antitumour Quinazoline Inhibitor of Thymidylate Synthetase: Synthesis, Biological Properties and Therapeutic Results in Mice," *European Journal of Cancer*, vol. 17, pp. 11–19 (1981).

Calvert et al., "A Phase I Evaluation of the Quinazoline Antifolate Thymidylate Synthase Inhibitor, $N^{10}$–Propargyl–5,8–Dideazafolic Acid, CB3717," *Journal of Clinical Oncology*, vol. 4, No. 8, pp. 1245–1252 (1986).

Hynes et al., "Synthesis of Analogs of 6–Arylthio–, 6–Arylsulfinyl–, and 6–Arylsulfonyl–2,4–diaminoquinazolines as Potential Antimalarial Agents," *Journal of Medicinal Chemistry*, vol. 17, No. 7, pp. 682–684 (1974).

Hynes et al., "Inhibition of Murine Thymidylate Synthase and Human Dihydrofolate Reductase by 5,8–Dideaza Analogues of Folic Acid and Aminopterin," *Journal of Medicinal Chemistry*, vol. 31, pp. 449–454 (1988).

Singh et al., "Synthesis of 5–Trifluoromethyl–5,8–dideazafolic Acid and 5–Trifluoromethyl–5,8–dideazaisofolic Acid," *Journal of Heterocyclic Chemistry*, vol. 27, pp. 2101–2105 (1990).

Jackman et al., "ICI D1694, a Quinazoline Antifolate Thymidylate Synthase Inhibitor That Is a Potent Inhibitor of L1210 Tumor Cell Growth In Vitro and In Vivo: A New Agent for Clinical Study," *Cancer Research*, vol. 51, pp. 5579–5586 (1991).

Marsham et al., "Quinazoline Antifolate Thymidylate Synthase Inhibitors: Bridge Modifications and Conformationally Restricted Analogues in the C2–Methyl Series," *Journal of Medicinal Chemistry*, vol. 34, pp. 2209–2218 (1991).

Taylor, et al., "Pyridine–1–Oxides. II. A New Synthesis of Ricinine," *Journal of Chemistry*, vol. 78 (1956), pp. 214–217.

Von Hoff, et al., "Prospective Clinical Trial of a Human Tumor Cloning System," *Cancer Research*, vol. 43 (1983), pp. 1926–1931.

(List continued on next page.)

*Primary Examiner*—Matthew V. Grumbling
*Attorney, Agent, or Firm*—Finnegan, Henderson, Farabow, Garrett & Dunner

[57] ABSTRACT

Quinazoline compounds which demonstrate antiproliferative activity, such as antitumor activity, processes of preparing these compounds, pharmaceutical compositions containing these compounds, and the use of these compounds. These compounds inhibit the growth and proliferation of the cells of higher organisms and microorganisms, such as bacteria, yeasts and fungi. Preferred quinazoline compounds are capable of inhibiting the enzyme thymidylate synthase. Effects derived from the inhibition of the enzyme thymidylate synthase include those discussed above.

6 Claims, No Drawings

OTHER PUBLICATIONS

Baker, et al., An Antimalarial Alkaloid from Hydrangea. XVI. Synthesis of 5–, 6–, 7–, and 8–Derivatives with Two Different Substituents, *Journal of Chemistry*, 1952, pp. 157–163.

Hertog, et al., "Reactivity of 4–Nitropyridine–N–Oxide," *Recueil*, vol. 70 (1951), pp. 581–589.

Kubo, et al., "Synthesis of 2–[[(4–Fluoroalkoxy–2–pyridyl)methyl]sulfinyl]1–H–benzimidasoles as Antiulcer Agents," *Chem. Pharm. Bulletin*, vol. 38, No. 10 (1990), pp. 2853–2858.

Ashimori, et al., "Novel 1,4–Dihydropyridine Calcium Antagonists. I. Synthesis and Hypotensive Activity of 4–(Substituted Pyridyl)–1,4–Dihydropyridine Derivatives," *Chem. Pharm. Bulletin*, vol. 38, No. 9 (1990), pp. 2446–2458.

V. Balasubramaniyam, *Chemical Reviews*, vol. 66, No. 6 (1966), pp. 567–641.

Webber et al., J. Med. Chem. (1993), 36(6), 733–46, Feb. 1993.

Crippen et al., J. Med. Chem., 22(8), 998–97, May 1979.

Ghose et al., J. Med. Chem., 25(8), 892–9, Feb. 1982.

Ghose et al., J. Med. Chem. 26(7) 996–1010, Feb. 1983.

ANTIPROLIFERATIVE QUINAZOLINES

This application is a divisional of U.S. patent application Ser. No. 08/418,415, field Apr. 7, 1995, now U.S. Pat. No. 5,707,992 which in turn is a cotinuation of U.S. patent application Ser. No. 07/861,030, field Mar. 31, 1992, now U.S. Pat. No. 5,430,148. These U.S. patent applications are entirely incorporated herein by reference.

FIELD OF THE INVENTION

The present invention relates to certain quinazoline compounds which demonstrate antiproliferative activity, such as antitumor activity, to processes for preparing these compounds, to pharmaceutical compositions containing these compounds, and to the use of these compounds to inhibit the growth and proliferation of the cells of higher organisms and microorganisms, such as bacteria, yeasts and fungi. Preferred compounds of the present invention are capable of inhibiting the enzyme thymidylate synthase. Effects derived from the inhibition of the enzyme thymidylate synthase include those discussed above.

BACKGROUND OF THE INVENTION

A large class of antiproliferative agents includes antimetabolite compounds. A particular subclass of antimetabolites known as antifolates or antifols are antagonists of the vitamin folic acid. Typically, antifolates closely resemble the structure of folic acid and incorporate the characteristic p-benzoyl glutamate moiety of folic acid. The glutamate moiety of folic acid takes on a double negative charge at physiological pH. Therefore, this compound and its analogues have an active, energy-driven transport system to cross the cell membrane and exert a metabolic effect. On the other hand, a compound without the glutamate group may passively diffuse into a cell.

A valid target for an antifolate is the enzyme thymidylate synthase. Thymidylate synthase catalyzes the C-methylation of 2'-deoxyuridylate ("dUMP") to provide 2'-deoxythymidylate ("dTMP"). This one-carbon transfer reaction is critical to cell division. Thus, a number of folate analogues have been synthesized and studied for their ability to inhibit the enzyme thymidylate synthase. A prototypic, specific, tight-binding inhibitor of thymidylate synthase, 10-propargyl-5,8-dideazafolic acid (T. R. Jones et al., "A Potent Antitumsor Quinazoline Inhibitor of Thymidylate Synthetase: Synthesis, Biological Properties and Therapeutic Results in Mice," *Eur. J. Cancer* 17:11 (1981)), has shown activity against ovarian, liver and breast cancer, with, however, troublesome hepatic and renal toxicities (A. H. Calvert et al., "A Phase I Evaluation of the Quinazoline Antifolate Thymidylate Synthase Inhibitor, N10-Propargyl-5,8-Dideazafolic Acid, CB3717," *J. Clin. Oncol.* 4:1245 (1986)). By addressing two properties in this class of molecule (solubility and capability for intracellular polyglutamation), a superior second generation analogue (ICI D1694) was developed.

Several lipophilic thymidylate synthase inhibitors have been developed recently. (See, e.g., E. M. Berman et al., "Substituted Quinazolinones as Anticancer Agents," U.S. Pat. No. 4,857,530; T. R. Jones et al., "Antiproliferative Cyclic Compounds," Copending U.S. patent application Ser. No. 07/432,338, which is a continuation application of Ser. No. 071251,765 filed Sep. 30, 1988; M. D. varney et al., "Antiproliferative Substituted Naphthalene Compounds," U.S. patent application Ser. No. 07/583,970 filed Sep. 17, 1990; S. H. Reich et al., "Antiproliferative Substituted Tricyclic Compounds," U.S. patent application Ser. No. 07/587,666 filed Sep. 25, 1990; L. R. Hughes et al., "Antitumour Agents," European Patent Application No. 373891, filed Dec. 12, 1989; and T. R. Jones et al., "Antifolate Quinazolines," U.S. patent application Ser. No. 07/812,274 filed Dec. 20, 1991).

SUMMARY OF THE INVENTION

The present invention relates to novel quinazoline compounds which demonstrate antiproliferative activity, such as antitumor activity. These compounds are effective in inhibiting the growth and proliferation of the cells of higher organisms and of microorganisms, such as bacteria, yeasts and fungi, processes for preparing these compounds, pharmaceutical compositions containing these compounds, and the use of these compounds. Preferred quinazoline compounds according to the present invention are capable of inhibiting the enzyme thymidylate synthase. Effects derived from the inhibition of the enzyme thymidylate synthase include those discussed above.

DETAILED DESCRIPTION OF THE INVENTION

The present invention relates to quinazoline compounds having the formula I

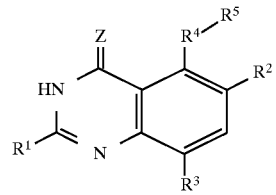

wherein:

$R^1$ represents hydrogen, halogen, alkyl, —OH, —O-alkyl, —O-(aryl or heteroaryl), —S-alkyl, —S-(aryl or heteroaryl), —NH$_2$, —NH-alkyl, —N-(alkyl)$_2$, —NHCHO, —NHOH, —NHO-alkyl, —NHNH$_2$, substituted —NHNH$_2$, —NHC(=NH)NH$_2$, —NHC(=NH)alkyl, fluoroalkyl, cycloalkyl, alkenyl, alkynyl, aryl, or heterocycle;

$R^2$ and $R^3$, which may be the same or different, represent hydrogen, halogen, alkyl, cycloalkyl, —OH, —O-alkyl, —S-alkyl, —NH$_2$, —NH-alkyl, —N-(alkyl)$_2$, —NHCHO, —NO$_2$, —NHOH, —NHO-alkyl, —NHNH$_2$, substituted —NHNH$_2$, —CN, —CO$_2$H, —CO$_2$-alkyl, —CONH$_2$, —CONH-alkyl, —CON(alkyl)$_2$, —CSNH$_2$, —CSNH-alkyl, —CSN(alkyl)$_2$, —C(=NH)NH$_2$, —NHC(=NH)NH$_2$, —NHC(=NH)alkyl, —SO-alkyl, —SO$_2$-alkyl, fluoroalkyl, —O-fluoroalkyl, —S-fluoroalkyl, —NHCO(alkyl), —NHCO(fluoroalkyl), —SO-fluoroalkyl, —SO$_2$-fluoroalkyl, —SH, —SO$_3$H, —SO$_2$NH$_2$, —SO$_2$NH(alkyl), —SO$_2$N(alkyl)$_2$, alkenyl, alkynyl, aryl, or heterocycle;

z represents O or S;

$R^4$ represents O, S, SO, SO$_2$, NH, N-alkyl, CH$_2$, CH-alkyl, CH-(aryl or heteroaryl), CHOH, CHO-alkyl, CHO-(aryl or heteroaryl), C(alkyl)$_2$, C(aryl or heteroaryl)$_2$, C(alkyl)(aryl or heteroaryl), CHS-alkyl, CHS-(aryl or heteroaryl), C(OH)(alkyl), C(OH)(aryl or heteroaryl), C(OH)(cycloalkyl), N(OH), N-cycloalkyl, N(aryl or heteroaryl), C(cycloalkyl)$_2$, C(aryl or heteroaryl)(cycloalkyl), C(alkyl)(alkenyl), C(alkyl)(alkynyl), C(alkenyl)$_2$, C(alkynyl)$_2$, C(alkynyl)(aryl or heteroaryl), C(alkynyl)(alkenyl), C(alkenyl)(aryl or heteroaryl), C(cycloalkyl)(alkenyl), C(cycloalkyl) (alkynyl), C(alkyl)(aryl or heteroaryl), CH(cycloalkyl), CH(alkenyl), CH(alkynyl), C(alkyl)(cycloalkyl), C(alkyl)(O-alkyl), C(alkenyl)(O-alkyl), C(alkynyl)(O-alkyl), C(alkyl)(O-cycloalkyl), C(alkenyl)(O-cycloalkyl), C(alkynyl)(O-cycloalkyl), C(aryl or heteroaryl)(O-alkyl), C(aryl or heteroaryl)(O-cycloalkyl), C(alkynyl)(S-alkyl), C(alkynyl)(S-cycloalkyl), C(alkenyl)(S-alkyl), C(alkenyl)(S-cycloalkyl), C(alkyl)(S-alkyl), C(alkyl)(S-cycloalkyl), C(aryl or heteroaryl)(S-alkyl), C(aryl or heteroaryl)(S-cycloalkyl), N(NH$_2$), N[NH(alkyl)], N[N(alkyl)$_2$], N[NH(cycloalkyl)], N[N(alkyl)(cycloalkyl)], CH(NH$_2$), CH[NH(alkyl)], CH[NH(cycloalkyl)], CH[N(alkyl)$_2$], CH[N(alkyl)(cycloalkyl)], CH[N(cycloalkyl)$_2$], C(alkyl)(NH$_2$), C(alkyl)[NH(alkyl)], C(alkyl)[N(cycloalkyl)$_2$], C(alkyl)[NH(cycloalkyl)], C(alkyl)[N(alkyl)$_2$], C(alkyl)[N(alkyl)(cycloalkyl)], C(aryl or heteroaryl)(NH$_2$), C(aryl or heteroaryl)]NH (alkyl)], C(aryl or heteroaryl)[NH(cycloalkyl)], C(aryl or heteroaryl)[N(alkyl$_2$], C(aryl or heteroaryl)[N(cycloalkyl)$_2$], or C(aryl or heteroaryl)[N(alkyl) (cycloalkyl)]; and R$^5$ represents a substituted or unsubstituted aryl or heteroaryl group.

As used herein, the language "capable of inhibiting the enzyme thymidylate synthase," or the like, refers to a compound having a thymidylate synthase inhibition constant ("TS K$_i$") of less than or equal to about 10$^{-4}$M. Preferred compounds according to the present invention have TS K$_i$ values in the range of less than about 10$^{-5}$M, more preferably less than about 10$^{-6}$M, and most preferably less than about 10$^{-7}$M.

Thymidylate synthase is merely exemplary of the activity of the quinazoline compounds of the present invention. Indeed, certain compounds may demonstrate an antifolate activity besides, or even in addition to, thymidylate synthase inhibition. Further, certain compounds may show antiproliferative activity stemming from a completely different locus of action than the inhibition of folic metabolic pathways.

Certain quinazoline compounds according to the present invention may possess one or more assymetric carbon atoms, and therefore may exist in racemic and optically active forms. The present invention thus is intended to encompass the racemic forms of the quinazoline compounds according to the present invention, as well as any optically active forms thereof, which possess a antitumor activity.

As used herein, the language "alkyl" includes both straight and branched alkyl groups. An analogous convention applies to other generic terms such as "alkenyl", "alkynyl" and the like. Furthermore, as used herein, the language "alkyl", "alkenyl", "alkynyl" and the like encompasses both substituted and unsubstituted groups.

The language "alkyl" refers to groups having one to eight, preferably one to six carbon atoms. For example, "alkyl" may refer to methyl, ethyl, n-propyl, isopropyl, butyl, isobutyl, sec-butyl, tert-butyl, pentyl, isopentyl tert-pentyl, hexyl, isohexyl, and the like. Suitable substituted alkyls include, but are not limited to, fluoromethyl, difluoromethyl, trifluoromethyl, 2-fluoroethyl, 3-fluoropropyl, hydroxymethyl, 2-hydroxyethyl, 3-hydroxypropyl, and the like.

The language "alkenyl" refers to groups having two to eight, preferably two to six carbon atoms. For example, "alkenyl" may refer to prop-2-enyl, but-2-enyl, but-3-enyl, 2-methylprop-2-enyl, hex-2-enyl, hex-5-enyl, 2,3-dimethylbut-2-enyl, and the like. The language "alkynyl," which also refers to groups having two to eight, preferably two to six carbons, includes, but is not limited to, prop-2-ynyl, but-2-ynyl, but-3-ynyl, pent-2-ynyl, 3-methylpent-4-ynyl, hex-2-ynyl, hex-5-ynyl, and the like.

The term "cycloalkyl" as used herein refers to groups having three to seven, preferably three to six carbon atoms. Suitable cycloalkyls include, but are not limited to cyclopropyl, cyclobutyl, cyclopentyl, cyclohexyl, cycloheptyl and the like. The language "heterocycle," which refers to groups having one or more heteroatoms, and preferably three to seven ring atoms total, includes, but is not limited to oxetane, tetrahydrofuranyl, tetrahydropyranyl, aziridine, azetidine, pyrrolidine, piperidine, morpholine, piperazine and the like.

The "halogen" substituent according to the present invention may be a fluoro, chloro, bromo or iodo substituent.

The language "aryl" and "heteroaryl," as used herein, refers to both monocyclic and polycyclic groups, which may be either substituted or unsubstituted. Examples of useful aryl ring groups include phenyl, 1,2,3,4-tetrahydronaphthyl, naphthyl, phenanthryl, anthryl, phenanthro and the like. Examples of typical heteroaryl rings include 5-membered monocyclic ring groups such as thienyl, pyrrolyl, imidazolyl, pyrazolyl, furyl, isothiazolyl, furazanyl, isoxazolyl, thiazolyl and the like; 6-membered monocyclic groups such as pyridyl, pyrazinyl, pyrimidinyl, pyridazinyl, triazinyl and the like; and polycyclic heterocyclic ring groups such as benzo[b]thienyl, naphtho[2,3-b] thienyl, thianthrenyl, isobenzofuranyl, chromenyl, xanthenyl, phenoxathienyl, indolizinyl, isoindolyl, indolyl, indazolyl, purinyl, isoquinolyl, quinolyl, phthalazinyl, naphthyridinyl, quinoxalinyl, quinazolinyl, benzothiazole, benzimidazole, tetrahydroquinoline cinnolinyl, pteridinyl, carbazolyl, beta-carbolinyl, phenanthridinyl, acridinyl, perimidinyl, phenanthrolinyl, phenazinyl, isothiazolyl, phenothiazinyl, phenoxazinyl, and the like.

As discussed above, the R$^1$ substituent of formula may be hydrogen, halogen, alkyl, —OH, —O-alkyl, —O-(aryl or heteroaryl), —S-alkyl, —S-(aryl or heteroaryl), —NH$_2$, —NH-alkyl, —N-(alkyl)$_2$, —NHCHO, —NHOH, —NHO-alkyl, —NHNH$_2$, substituted —NHNH$_2$, —NHC(=NH) NH$_2$, —NHC(=NH)alkyl, fluoroalkyl, cycloalkyl, alkenyl, alkynyl, aryl, or heterocycle. The R$^1$ substituent is preferably a methyl or amino group.

The R$^2$ and R$^3$ substituents of formula I according to the present invention, which may be the same or different, may be hydrogen, halogen, alkyl, cycloalkyl, —OH, —O-alkyl, —S-alkyl, —NH$_2$, —NH-alkyl, —N-(alkyl)$_2$, —NHCHO, —NO$_2$, —NHOH, —NHO-alkyl, —NHNH$_2$, substituted —NHNH$_2$, —CN, —CO$_2$H, —CO$_2$-alkyl, —CONH$_2$, —CONH-alkyl, —CON(alkyl)$_2$, —CSNH$_2$, —CSNH-alkyl, —CSN(alkyl)$_2$, —C(=NH)NH$_2$, —NHC(=NH)NH$_2$, —NHC(=NH)alkyl, —SO-alkyl, —SO$_2$-alkyl, fluoroalkyl, —O-fluoroalkyl, —S-fluoroalkyl, —NHCO(alkyl), —NHCO(fluoroalkyl), —SO-fluoroalkyl, —SO$_2$-fluoroalkyl, —SH, —SO$_3$H, —SO$_2$NH$_2$, —SO$_2$NH(alkyl), —SO$_2$N(alkyl)$_2$, alkenyl, alkynyl, aryl, or heterocycle.

The R$^2$ substituent is preferably hydrogen or a methyl, ethyl, hydroxy, methoxy, chloro or trifluoromethyl group. More preferably, R$^2$ is hydrogen or a methyl, chloro or trifluoromethyl group. The R$^3$ substituent is preferably hydrogen.

The Z substituent of formula I according to the present invention is either oxygen or sulfur. In a preferred embodiment, the Z substituent is oxygen.

The R$^4$ substituent of formula I according to the present invention may be C=O, oxygen, sulfur, SO, SO$_2$, NH, N-alkyl, CH$_2$, CH-alkyl, CH-(aryl or heteroaryl), CHOH, CHO-alkyl, CHO-(aryl or heteroaryl), C(alkyl)$_2$, C(aryl or heteroaryl)$_2$, C(alkyl)(aryl or heteroaryl), CHS-alkyl, CHS-aryl, C(OH)(alkyl), C(OH)(aryl or heteroaryl), C(OH)(cycloalkyl), N(OH), N-cycloalkyl, N(cycloalkyl)SO$_2$, N(aryl or heteroaryl), C(cycloalkyl)$_2$, C(aryl or heteroaryl)(cycloalkyl), C(alkyl)(alkenyl), C(alkyl)(alkynyl), C(alkenyl)$_2$, C(alkynyl)$_2$, C(alkynyl)(aryl or heteroaryl), C(alkynyl)(alkenyl), C(alkenyl)(aryl or heteroaryl), C(cycloalkyl)(alkenyl), C(cycloalkyl)(alkynyl), C(alkyl)(aryl or heteroaryl), CH(cycloalkyl), CH(alkenyl), CH(alkynyl), C(alkyl)(cycloalkyl), C(alkyl)(O-alkyl), C(alkenyl)(O-alkyl), C(alkynyl)(O-alkyl), C(alkyl)(O-cycloalkyl), C(alkenyl)(O-cycloalkyl), C(alkynyl)(O-cycloalkyl), C(aryl or heteroaryl)(O-alkyl), C(aryl or heteroaryl)(O-cycloalkyl), C(alkynyl)(S-alkyl), C(alkynyl)(S-cycloalkyl), C(alkenyl)(S-alkyl), C(alkenyl)(S-cycloalkyl), C(alkyl)(S-alkyl), C(alkyl)(S-cycloalkyl), C(aryl or heteroaryl)(S-alkyl), C(aryl or heteroaryl)(S-cycloalkyl), N(NH$_2$), N[NH(alkyl)], N[N(alkyl)$_2$], N[NH(cycloalkyl)], N[N(alkyl)(cycloalkyl)], CH(NH$_2$), CH[NH(alkyl)], CH[NH(cycloalkyl)], CH[N(alkyl)$_2$], CH[N(alkyl)(cycloalkyl)], CH[N(cycloalkyl)$_2$], C(alkyl)(NH$_2$) C(alkyl)[NH(alkyl)], C(alkyl)[N(cycloalkyl)$_2$], C(alkyl)[NH(cycloalkyl)], C(alkyl)[N(alkyl)$_2$], C(alkyl)[N(alkyl)(cycloalkyl)], C(aryl or heteroaryl)(NH$_2$), C(aryl or heteroaryl)NH(alkyl)], C(aryl or heteroaryl)[NH(cycloalkyl)], C(aryl or heteroaryl)[N(alkyl$_2$], C(aryl or heteroaryl)[N(cycloalkyl)$_2$], or C(aryl or heteroaryl)[N(alkyl)(cycloalkyl)].

The $R^4$ substituent is preferably oxygen, sulfur or a methylene, C=O, NH, NCH$_3$, CH(OH) or C(OH)(phenyl) group. More preferably, the $R^4$ substituent is sulfur.

The $R^5$ substituent of formula I can be any one of a large number of aryl or heteroaryl ring compounds, including, but not limited to, the aryl and heteroaryl rings discussed previously. The $R^5$ substituent may be unsubstituted or substituted. Suitable substituents for $R^5$ include a wide variety of electron-donating and electron-withdrawing substituents. As used herein, the language "electron-withdrawing" includes, but is not limited to, groups such as —NO$_2$; —CF$_3$; —CN; carboxy; halogen; —SO$_2R^6$, wherein $R^6$ is an alkyl, aryl or heteroaryl group as discussed above, or $R_6$ is an —NR$_7$R$_8$ group, wherein R$_7$ and R$_8$ represent alkyl groups; and the like. The language "electron-donating" includes, but is not limited to, groups such as —NH$_2$; —NH-(alkyl); —NHOH; —NHNH$_2$; —O-(alkyl); —S-(alkyl); —NR$^7$R$^8$, wherein R$^7$ and R$^8$ represent alkyl groups; and the like.

Typical substituents for $R^5$ include halogen, hydroxy, alkoxy, alkyl, hydroxyalkyl, fluoroalkyl, amino, —NH-(alkyl), —N-(alkyl)$_2$, —CO-amino acid, —CN, —NO$_2$, —CF$_3$, carbalkoxy, carbamyl, carbonyl, carboxy, amino acid carbonyl, —SO$_2$NHCO, SO$_2$-amino acid, amino acid sulfonyl, sulfamyl, sulfanilyl, sulfhydryl, sulfino, sulfinyl, sulfo, sulfonamido, sulfonyl, (alkyl)-thio, substituted or unsubstituted phenylsulfonyl, phenylmercapto, phosphazo, phosphinico, phosphino, phospho, phosphono, phosphoro, phosphoroso, mercaptoaryl, and the like.

Particularly preferred structures for $R^5$ include:

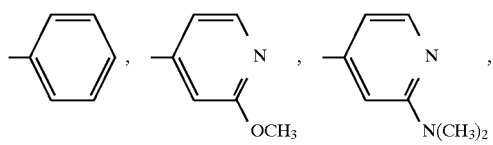

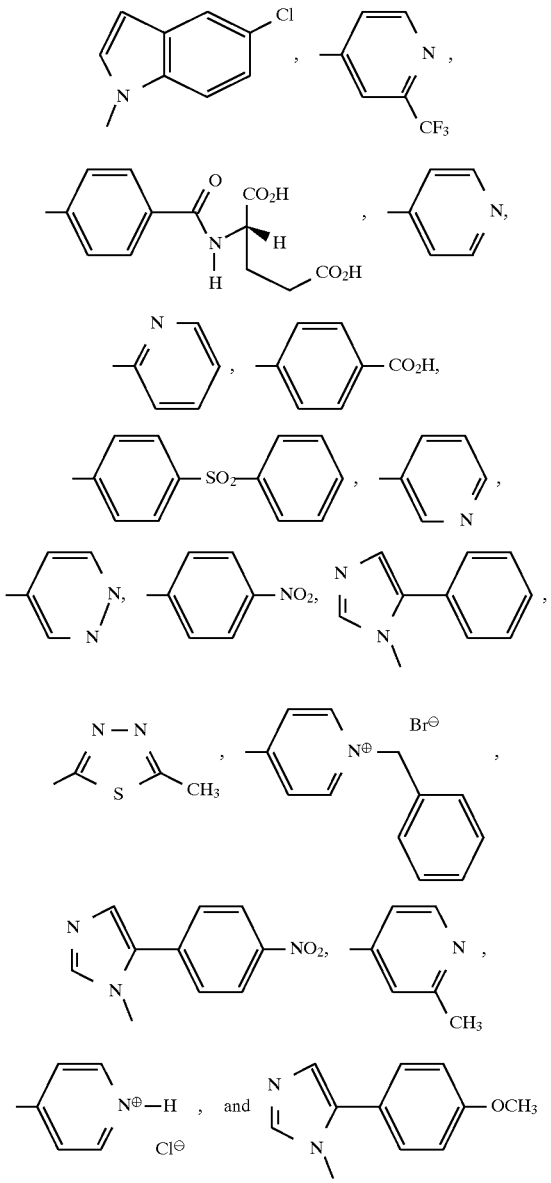

A preferred class of compounds according to the present invention includes those compounds according to formula I, wherein $R^3$ is hydrogen. Particularly preferred compounds of this class are those wherein Z is oxygen.

Another preferred class of compounds according to the present invention includes those compounds according to formula I, wherein $R^3$ is hydrogen and $R^1$ is either a methyl or amino group. Particularly preferred compounds of this class are those wherein Z is oxygen.

Another preferred class of compounds according to the present invention includes those compounds according to formula I, wherein $R^3$ is hydrogen and $R^2$ is hydrogen or a methyl, ethyl, hydroxy or methoxy group. More preferably, $R^2$ is hydrogen or a methyl group. Particularly preferred compounds of this class are those wherein Z is oxygen.

Another preferred class of compounds according to the present invention includes those compounds according to formula I, wherein $R^3$ is hydrogen and $R^4$ is oxygen, sulfur or a methylene, C=O, CH(OH) or C(OH)(phenyl) group. More preferably, $R^4$ is sulfur. Particularly preferred compounds of this class are those wherein Z is oxygen.

Another preferred class of compounds according to the present invention includes those compounds according to formula I, wherein $R^3$ is hydrogen and $R^5$ is one of the following:

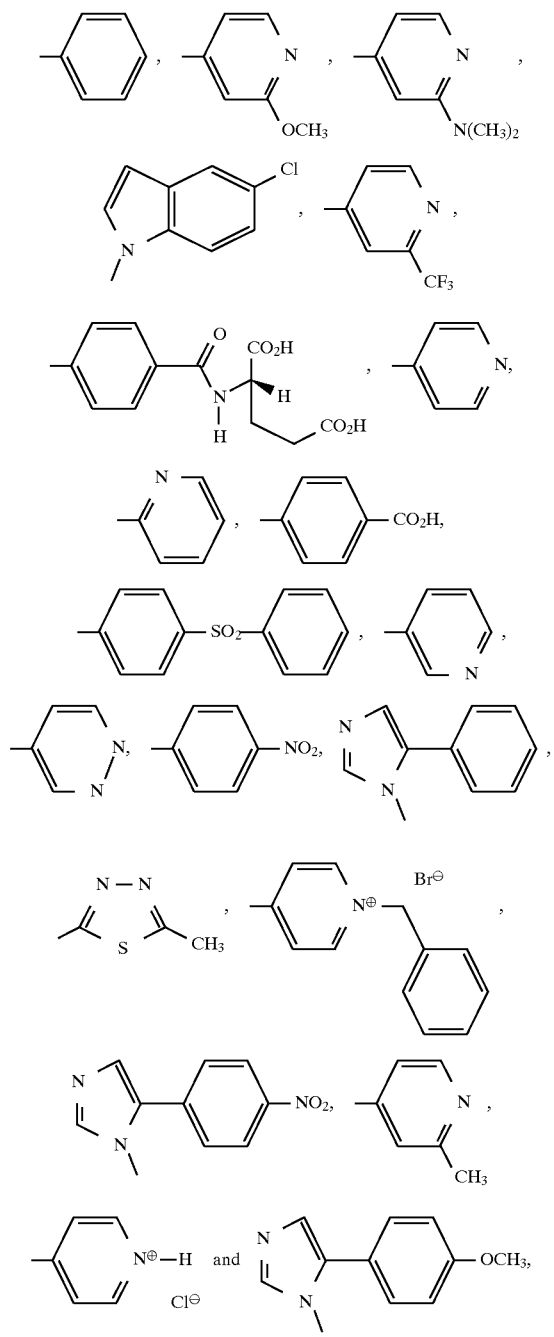

Particularly preferred compounds of this class are those wherein Z is oxygen.

Another preferred class of compounds according to the present invention includes those compounds according to formula I, wherein $R^3$ is hydrogen, $R^1$ is either a methyl or amino group, $R^2$ is hydrogen or a methyl, ethyl, hydroxy or methoxy group, $R^4$ is oxygen, sulfur or a methylene, C=O, CH(OH) or C(OH)(phenyl) group, and $R^5$ is one of the following:

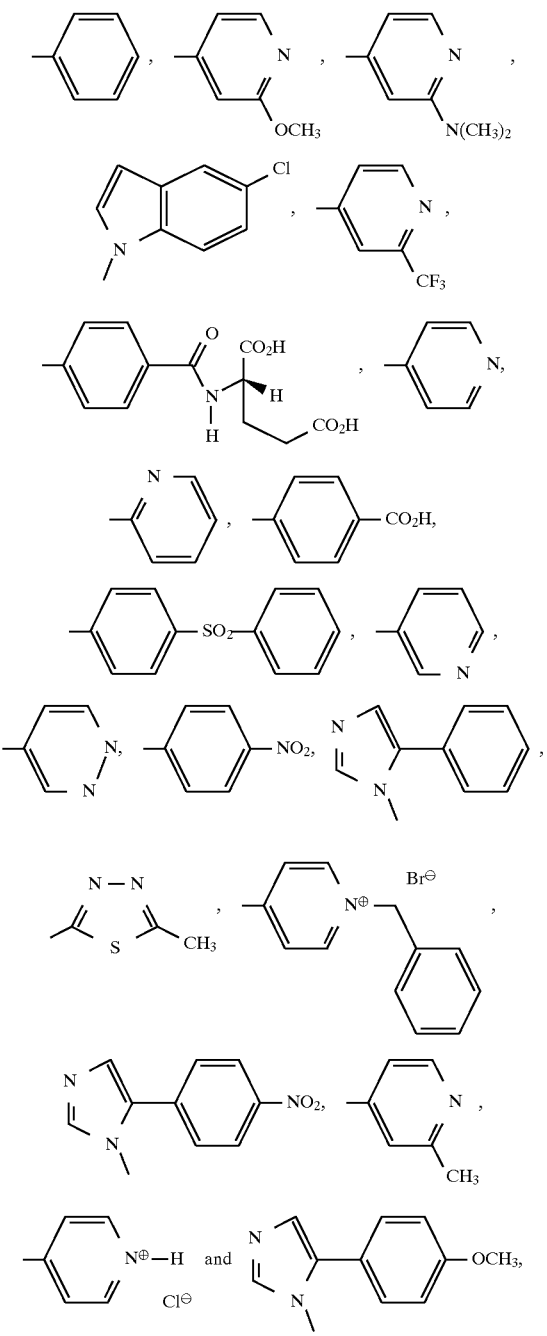

Particularly preferred compounds of this class are those wherein Z is oxygen.

According to a preferred embodiment of the present invention, $R^3$ is hydrogen, $R^1$ is either a methyl or amino group, $R^2$ is hydrogen or a methyl group, $R^4$ is sulfur and $R^5$ is one of the rings disclosed in the preceding paragraph. Particularly preferred compounds of this class are those wherein Z is oxygen.

Particularly preferred compounds according to the present invention are illustrated in Table 1 below. Compounds 14A, 24A and 25A are especially preferred.

TABLE 1
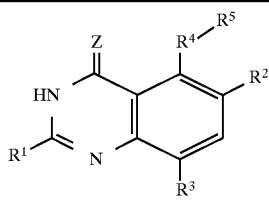
wherein R³ is H, and
| | R¹ | R² | R⁴ | R⁵ |
|---|---|---|---|---|
| 1A) | CH₃ | H | O | Ph |
| 2A) | CH₃ | H | S | Ph |
| 3A) | CH₃ | H | CH₂ | 5-chloro-1-methylindol-3-yl |
| 4A) | CH₃ | H | C=O | Ph |
| 5A) | CH₃ | H | CH(OH) | Ph |
| 6A) | CH₃ | H | C(OH)(Ph) | Ph |
| 7A) | CH₃ | H | S | pyridin-4-yl |
| 8A) | CH₃ | CH₃ | S | pyridin-4-yl |
| 9A) | CH₃ | CH₃ | S | 4-(phenylsulfonyl)phenyl |
| 10A) | CH₃ | CH₃ | S | 4-nitrophenyl |
| 11A) | CH₃ | CH₃ | S | 5-methyl-1,3,4-thiadiazol-2-yl |
| 12A) | CH₃ | CH₃ | S | 2-methylpyridin-4-yl |

TABLE 1-continued
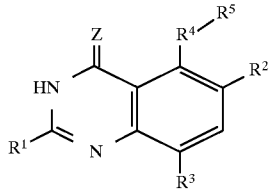
wherein R³ is H, and
| | R¹ | R² | R⁴ | R⁵ |
|---|---|---|---|---|
| 13A) | CH₃ | OCH₃ | S | 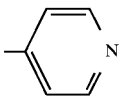 |
| 14A) | NH₂ | CH₃ | S | 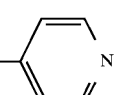 |
| 15A) | CH₃ | OH | S | 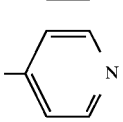 |
| 16A) | CH₃ | CH₃ | S | 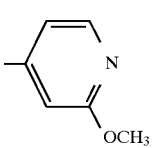 |
| 17A) | CH₃ | CH₃ | S | 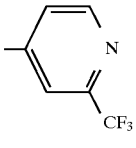 |
| 18A) | NH₂ | CH₃ | S | 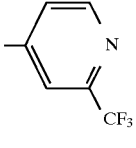 |
| 19A) | CH₃ | CH₂CH₃ | S | 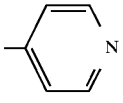 |
| 20A) | CH₃ | H | S | 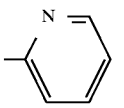 |
| 21A) | CH₃ | CH₃ | S | 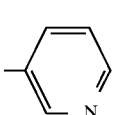 |
| 22A) | CH₃ | H | S | 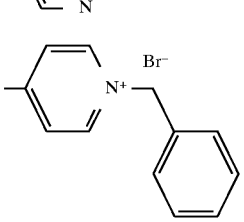 |

TABLE 1-continued
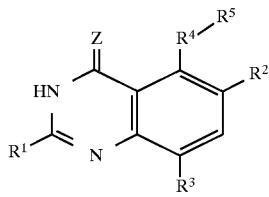
wherein R³ is H, and
| | R¹ | R² | R⁴ | R⁵ |
|---|---|---|---|---|
| 23A) | CH₃ | CH₃ | S | 4-pyridinium chloride |
| 24A) | NH₂ | CH₃ | S | 4-pyridinium chloride |
| 25A) | | | | (structure shown: 3-(4-pyridiniumthio)-2-methyl-6-guanidinium benzamide, 2 Cl⁻) |
| 26A) | CH₃ | CH₃ | S | 2-(dimethylamino)-4-pyridyl |
| 27A) | CH₃ | CH₃ | S | 4-[(N-glutamyl)carbonyl]phenyl |
| 28A) | CH₃ | CH₃ | S | 4-carboxyphenyl |
| 29A) | CH₃ | CH₃ | S | 4-pyridazinyl |
| 30A) | NH₂ | CH₃ | S | 4-pyridazinyl |
| 31A) | CH₃ | H | CH₂ | 1-methyl-5-phenyl-imidazol-4-yl |

TABLE 1-continued wherein $R^3$ is H, and

| | $R^1$ | $R^2$ | $R^4$ | $R^5$ |
|---|---|---|---|---|
| 32A) | $CH_3$ | H | $CH_2$ | 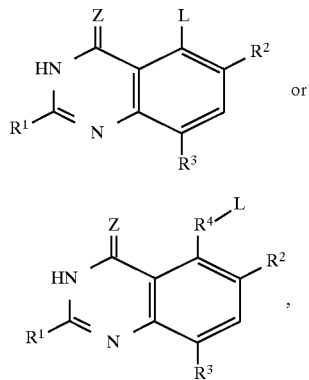 |
| 33A) | $CH_3$ | H | $CH_2$ | |

Another aspect of the present invention relates to processes of making the antiproliferative quinazoline compounds according to formula I.

One process according to the present invention for preparing quinazoline compounds of the formula I, comprises subjecting a compound of the formula (i)

or (ii)

wherein Z and $R^1$ to $R^3$ have the same meanings as described previously and L is a leaving group, to a displacement reaction with the appropriate compound to cause the leaving group L to be replaced with the desired $—R^4—R^5$ substituent in case (i) or with the appropriate $R^5$ substituent in case (ii). The process can be carried out under widely varying conditions, but is typically carried out in the presence of an appropriate base, solvent and catalyst at a temperature varying from about 70° C. to about 165° C., preferably from about 80° C. to about 140° C., and most preferably at from about 90° C. to about 100° C.

Leaving groups suitable for use in the process described above, as well as for use in other processes according to the present invention, include halogen atoms such as Br, Cl, F and I.

A preferred process for making antiproliferative quinazoline compounds according to formula I, wherein Z and $R^1$—$R^5$ have the same meanings as described previously, comprises the steps of:

(1) reacting a compound having the formula

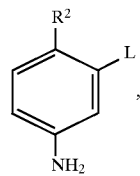

wherein L is a leaving group, for example, a halogen atom such as Br, Cl, F and I, and $R^2$ has the same meaning as described previously, with hydroxylamine hydrochloride and chloral hydrate to form an isonitrosoacetanilide compound of the formula

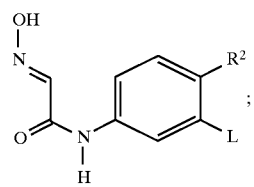

(2) treating the isonitrosoacetanilide compound of step (1) with sulfuric acid, followed by ice and purification with ethanol to obtain an isatin compound of the formula

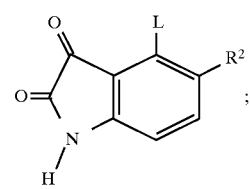

(3) reacting the isatin compound of step (2) with an aqueous basic peroxide, such as an aqueous NaOH and H$_2$O$_2$ solution, to form an anthranilic acid compound of the formula

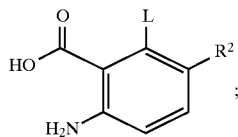

(4) reacting the anthranilic acid compound of step (3) with acetic anhydride to form an acetylanthranil compound of the formula

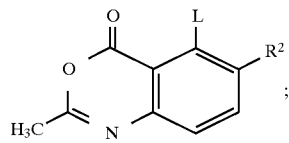

(5) reacting the acetylanthranil compound of step (4) with anhydrous ammonia, followed by NaOH and then by hydrochloric acid to obtain a quinazoline of the formula

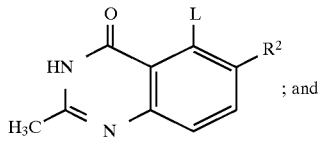

(6) subjecting the quinazoline compound of step (5) to a displacement reaction to replace the leaving group L with one of the desired R$^4$—R$^5$ substituents described previously, and thus obtain a compound according to fomula I.

Step (1) can be carried out under widely varying conditions, but is typically carried out in the presence of water, chloral hydrate, hydrochloric acid, sodium sulfate and hydroxyl amine hydrochloride at a temperature varying from about 0° C. to about 100° C., preferably from about 20° C. to about 100° C., and most preferably at about 100° C.

Step (2) can be carried out under widely varying conditions, but is typically carried out in the presence of concentrated H$_2$SO$_4$ at a temperature varying from about 50° C. to about 100° C., preferably from about 65° C. to about 100° C., and most preferably at about 80° C.

Step (3) can be carried out under widely varying conditions, but is typically carried out in the presence of water, sodium hydroxide and hydrogen peroxide at a temperature varying from about 0° C. to about 80° C., preferably from about 20° C. to about 80° C., and most preferably at about 80° C.

Step (4) can be carried out under widely varying conditions, but is typically carried out in the presence of acetic anhydride at a temperature varying from about 70° C. to about 140° C., preferably from about 100° C. to about 140° C., and most preferably at about 140° C.

Step (5) can be carried out under widely varying conditions, but is typically carried out in the presence of ammonia at a temperature varying from about −33° C. to about 20° C., preferably at about 20° C.

Step (6) can be carried out under widely varying conditions, but is typically carried out in the presence of an appropriate base, solvent and catalyst at a temperature varying from about 70° C. to about 165° C., preferably from about 80° C. to about 140° C., and most preferably at from about 90° C. to about 100° C.

A modification to the six step process discussed above, comprises the alternate steps of:

(5a) treating the acetylanthranil compound of step (4) with MeOH, followed by hydrochloric acid, to obtain a compound of the formula:

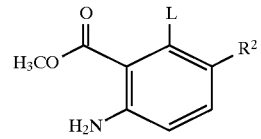

, or (5a') treating the anthranilic acid of step (3) with phosgene or triphosgene to form a compound of the formula:

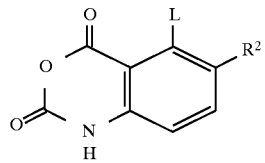

which is further treated with methanol;

(5b) reacting the product of step (5a) or (5a') with chloroformamidine hydrochloride to obtain a quinazoline compound of the formula:

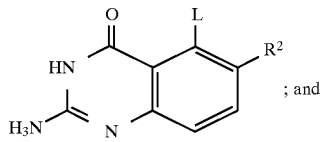

then subjecting the resulting quinazoline compound to a displacement reaction as set forth in step (6) discussed above to obtain a compound according to formula I.

Step (5a) can be carried out under widely varying conditions, but is typically carried out (i)in the presence of methanol at a temperature varying from about 0° C. to about 100° C., preferably from about 20° C. to about 70° C., and most preferably at about 70° C., and then (ii) in the presence of concentrated hydrochloric acid at a temperature varying from about 70° C. to about 100° C., more preferably at about 100° C.

Step (5a') can be carried out under widely varying conditions, but is typically carried out (i) in the presence of triphosgene at a temperature varying from about 0° C. to about 20° C., and then (ii) in the presence of methanol at a temperature varying from about 0° C. to about 70° C., more preferably at a temperature of from about 0° C. to about 20° C., and most preferably at about 20° C.

Step (5b) can be carried out under widely varying conditions, but is typically carried out in the presence of diglyme and chloroformamidine hydrochloride at a temperature varying from about 100° C. to about 175° C., preferably from about 160° C. to about 175° C., and most preferably at about 170° C.

In a particularly preferred embodiment of the six step process discussed above, step (6) is carried out by reacting the product of either step (5) or step (5b) with a 4-thiopyridine anion, in the presence of sodium hydride, copper (I) bromide and copper (I) oxide. A preferred process for preparing the anions of 4-thiopyridines for use in the present invention comprises reacting 4-mercaptopyridine with NaH in anhydrous N,N-Dimethylacetamide. The process of preparing the 4-thiopyridines may be carried out under widely varying conditions, but is typically carried out in the presence of sodium hydride and dimethylformamide at a temperature varying from about −20° C. to about 20° C., preferably from about 0° C. to about 20° C., and most preferably at about 20° C.

Another particularly preferred process according to the present invention for preparing quinazoline compounds of formula I, comprises the steps of:

(1) reacting a compound of the formula

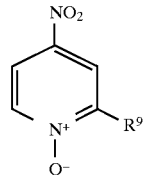

wherein the $R^9$ substituent is hydrogen, —CH$_3$, —OCH$_3$, CF$_3$, N(CH$_3$)$_2$, and the like, with a benzylmercaptan to form a compound of the formula

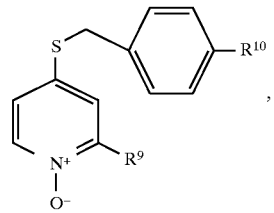

wherein the $R^{10}$ substituent is hydrogen, or —OCH$_3$;

(2) reducing the product of step (1);

(3) deprotecting the product of step (2); and (4) reacting the product of step (3) with a compound of the formula

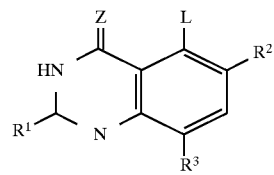

wherein Z and $R^1$ to $R^3$ have the same meanings as discussed previously and L is a leaving group, to obtain a compound of the formula

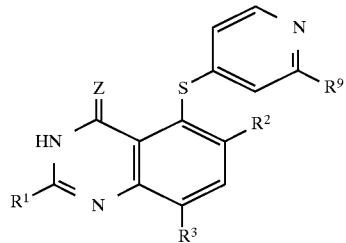

Step (1) according to this process can be carried out under widely varying conditions, but is typically carried out in the presence of an appropriate base and solvent at a temperature varying from about 0° C. to about 80° C., preferably from about 0° C. to about 20° C.

Step (2), the reducing step, can be carried out under widely varying conditions, but is typically carried out in the presence of PCl$_3$ and CHCl$_3$ at a temperature of from about 0° C. to about 80° C., preferably from about 20° C. to about 80° C., and more preferably at about 20° C.

Step (3), the deprotection step, can be carried out under widely varying conditions, but is typically carried out in the presence of an appropriate solvent and metal or metal salt at a temperature varying from about −78° C. to about 20° C., preferably from about −78° C. to about 0° C., and most preferably at from about −33° C. to about 0° C.

Step (4) can be carried out under widely varying conditions, but is typically carried out in the presence of dimethyl acetamide, sodium hydride, copper (I) bromide and copper (I) oxide at a temperature varying from about 70° C. to about 165° C., preferably from about 90° C. to about 100° C., and most preferably at about 90° C.

An alternative to the four step process discussed above comprises the steps of:

(1) reducing a compound of the formula

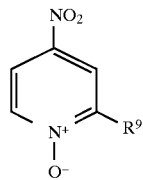

to form a compound of the formula

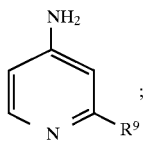

(2) reacting the product of step (1) with a xanthate compound to obtain a compound of the formula

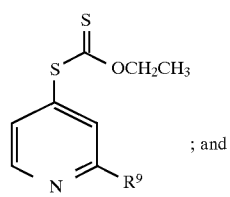

; and (3) subjecting the product of step (2) to hydrolysis and further reaction with a compound of the formula

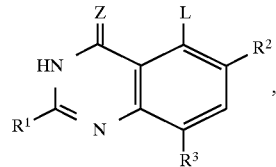

wherein Z and $R^1$ to $R^3$ have the same meanings discussed previously and L is a leaving group, in the presence of N,N-Dimethylacetamide, copper (I) bromide and copper (I) oxide to obtain a compound of the formula

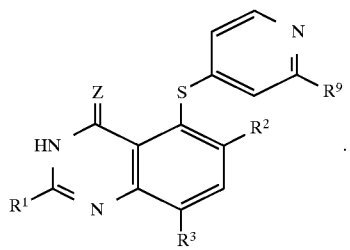

Step (1), the reducing step, can be carried out under widely varying conditions, but is typically carried out in the presence of hydrogen gas, an appropriate solvent and a catalytic amount of palladium, preferably at room temperature of about 20° C. Of course, elevated temperatures may be used in some cases to expedite the reaction.

Step (2) can be carried out under widely varying conditions, but is typically carried out in the presence of an aqueous acid and $NaNO_2$ followed by potassium xanthate, at a temperature varying from about −40° C. to about 20° C., preferably from about 0° C. to about 5° C., and most preferably at about 0° C.

The hydrolysis part of step (3) can be carried out under widely varying conditions, but is preferably carried out with $NaOH/CH_3OH$ at a temperature of from about 0° C. to about 20° C. The reaction part of step (3) following hydrolysis also may be carried out under widely varying conditions, but is typically carried cut in the presence of an appropriate base, solvent and catalyst, at a temperature varying from about 70° C. to about 165° C., preferably from about 90° C. to about 100° C., and most preferably at about 90° C.

Another preferred process for preparing the quinazoline compounds of formula I, wherein Z and $R^1$ to $R^5$ have the same meanings as described previously, comprises the steps of:

(1) reacting a compound of the formula

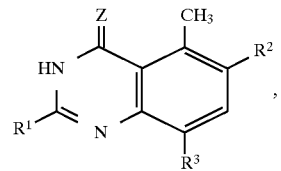

wherein $R^1$ to $R^3$ have the same meanings as described previously, with a compound suitable for providing a protecting group P, to form a compound of the formula

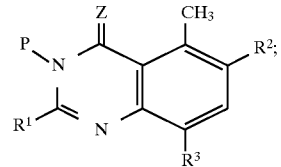

(2) converting the product of step (1) to a compound of the formula

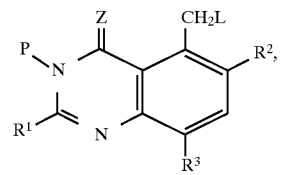

wherein L is a leaving group;

(3) subjecting the quinazoline compound of step (2) to a displacement reaction to form a compound of the formula

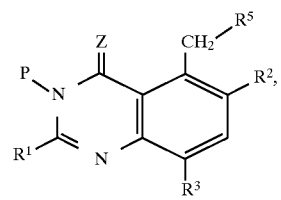

wherein $R^5$ has the same meaning as described previously; and (4) deprotecting the product of step (3).

Step (1) of the process described above can be carried out under widely varying conditions, but is typically carried out in the presence of the appropriate alkyl or acyl halide, a base and a solvent at a temperature varying from about 0° C. to about 20° C., preferably at about 20° C.

Although a variety of substituents may be used as protecting group P in the process described above, protecting group P is preferably a $CH_2OCH_2CH_2Si(CH_3)_3$, $CH_2OCH_3$, $CH_2OC(O)^tBu$ or $CO^tBu$ group. According to a preferred embodiment, P is $CH_2OCH_2CH_2Si(CH_3)_3$.

Step (2), the converting step, can be carried out under widely varying conditions to provide a wide variety of leaving groups, but is preferably carried out in the presence of N-Bromosuccinimide, bromine, N-Chlorosuccinimide or N-Iodosuccinimide, at a temperature varying from about 20° C. to about 100° C., preferably from about 50° C. to about 100° C., and most preferably at about 80° C. In a preferred embodiment, the process is carried out in the presence of N-Bromosuccinimide, $CCl_4$ and light.

Step (3) also can be carried out under widely varying conditions, but is typically carried out in the presence of an appropriate nucleophile, base and solvent, at a temperature varying from about 0° C. to about 150° C., preferably from about 20° C. to about 100° C., and most preferably at about 20° C.

In a preferred embodiment of this process, step (3) is carried out by reacting the product of step (2) with NaOEt (sodium ethoxide) and 2-nitropropane, followed by phenylmagnesium, to form a compound of the formula

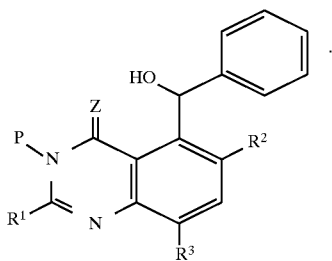

In another preferred embodiment, step (3) is carried out by reacting the product of step (2) with 5-chloroindole.

Step (4), which also can be carried out under widely varying conditions, is typically carried out in the presence of an appropriate acid or basic fluoride, at a temperature varying from about 0° C. to about 100° C., preferably from about 20° C. to about 100° C., and most preferably at about 20° C.

The materials and conditions used in deprotecting step (4) depend upon a variety of factors. Of course, the particular substituent used as protecting group P is one factor. For example, when P is a $CH_2OCH_2CH_2Si(CH_3)_3$ group, step (4) is preferably carried out by reacting the product of step (3) with tetrabutylammonium fluoride.

In a modification of the process described above, prior to deprotecting step (4), the product of step (3) is oxidized to form a compound of the formula

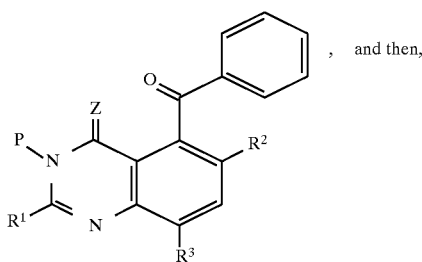

, and then, subsequent to deprotecting step (4), the product of step (4) is reacted with phenyllithium to form a compound of the formula

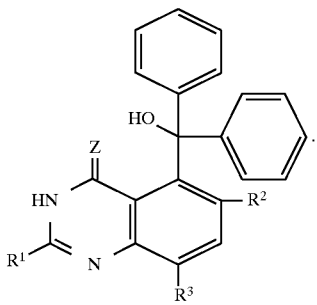

As illustrated above, it may be necessary to provide protecting groups either before, after or during the course of preparing the compounds according to the present invention.

A suitable protecting group for a ring nitrogen, such as may be included in a heteroaryl group, is for example, a pivaloyloxymethyl group, which may be removed by hydrolysis with a base such as sodium hydroxide; a tert-butyloxycarbonyl group, which may be removed by hydrolysis with an acid, such as hydrochloric acid or trifluoroacetic acid, or with a base such as tetra-n-butylammonium fluoride ("TBAF") or lithium hydroxide; a methoxymethyl group, which may be removed by hydrochloric acid and p-Toluenesulfonic acid; or a 2-(trimethylsilyl)ethoxymethyl group, which may be removed by TBAF or with an acid such as hydrochloric acid.

A suitable protecting group for a hydroxyl group is, for example, an esterifying group such as an acetyl or benzoyl group, which may be removed by hydrolysis with a base such as sodium hydroxide. Alternatively, when other groups present in the starting material do not contain an alkenyl or alkynyl group, the protecting group may be, for example, an alpha-arylalkyl group such as a benzyl group, which may be removed by hydrogenation in the presence of a catalyst such as palladium on charcoal or Raney nickel. An additional protecting group for a hydroxyl group is a group such as t-butyldiphenylsilyl ($—Si-t-Bu-Ph_2$), which may be removed by treatment with TBAF.

A suitable protecting group for a mercapto group is, for example, an esterifying group such as an acetyl group, which may be removed by hydrolysis with a base such as sodium hydroxide.

A suitable protecting group for an amino group may be, for example, an alkylcarbonyl group such as an acetyl group ($CH_3CO—$), which may be removed by treatment with an aqueous inorganic acid such as nitric, sulfuric or hydrochloric acid. Another protecting group for an amino group is an alkoxycarbonyl group such as a methoxycarbonyl or a tert-butyloxycarbonyl group. These groups may be removed by treatment with an organic acid such as trifluoroacetic acid.

A suitable protecting group for a primary amino group is, for example, an acetyl group, which may be removed by treatment with an aqueous inorganic acid such as nitric, sulfuric, or hydrochloric acid, or a phthaloyl group, which may be removed by treatment with an alkylamine such as dimethylaminopropylamine or with hydrazine.

A suitable protecting group for a carboxy group may be an esterifying group, for example, a methyl or an ethyl group, which may be removed by hydrolysis with a base such as sodium hydroxide. Another useful protecting group is a tert-butyl group, which may be removed by treatment with an organic acid such as trifluoroacetic acid.

While particularly preferred processes for preparing the antiproliferative compounds according to the present invention have been described in detail, it will be apparent to one skilled in the art that various other processes as well as changes and modifications to the disclosed processes can be used to prepare the compounds of the present invention.

The antiproliferative quinazoline compounds of the present invention, which may be employed in the pharmaceutical compositions according to the present invention, include all of those compounds described above, as well as pharmaceutically acceptable salts of these compounds. Pharmaceutically acceptable acid addition salts of the compounds of the invention containing a basic group are formed, where appropriate, with strong or moderately strong organic or inorganic acids in the presence of a basic amine by methods known in the art. Exemplary of the acid addition salts which are included in this invention are: (1) organic acid salts such as maleate, fumarate, lactate, oxalate, methanesulfonate, ethanesulfonate, benzenesulfonate, tartrate, glucuronate, citrate, and acetate; and (2) inorganic acid salts such as hydrobromide, hydrochloride, hydrosulfate, phosphate and nitrate salts. Pharmaceutically acceptable base addition salts of compounds of the invention containing an acidic group are prepared by known methods from organic and inorganic bases, and include nontoxic alkali metal and alkaline earth bases, for example, calcium, sodium and potassium hydroxides; ammonium hydroxides; and nontoxic organic bases such as triethylamine, butylamine, piperazine and tri(hydroxymethyl)-methylamine.

As stated above, the compounds of the invention possess antivroliferative activity, a property which may express itself in the form of antitumor activity. A compound of the invention may be active per se or it may be a pro-drug that is converted in vivo to an active compound. Preferred compounds of the invention are active in inhibiting the enzyme thymidylate synthase. Particularly preferred compounds are active in inhibiting the growth of the L1210 cell line, a mouse leukemia cell line which can be grown in tissue culture. Such compounds of the invention are also active in inhibiting the growth of bacteria such as *Escherichia coli* gram negative bacteria which can be grown in culture. The compounds of the invention may also be active inhibiting the growth of bacteria.

The antiproliferative compounds according to the present invention, as well as the pharmaceutically acceptable salts thereof, may be incorporated into convenient dosage forms such as capsules, tablets, or injectable preparations. Solid or liquid pharmaceutically acceptable carriers may be employed. Solid carriers include starch, lactose, calcium sulfate dihydrate, terra alba, sucrose, talc, gelatin, agar, pectin, acacia, magnesium stearate and stearic acid. Liquid carriers include syrup, peanut oil, olive oil, saline and water.

Similarly, the carrier or diluent may include any prolonged release materiel, such as glyceryl monostearate or glyceryl distearate, alone or with wax. When a liquid carrier is used, the preparation may be in the form of a syrup, elixir, emulsion, soft gelatin capsule, sterile injectable liquid (e.g. solution), such as an ampoule, or an aqueous or nonaqueous liquid suspension.

The pharmaceutical preparations are made following conventional techniques of a pharmaceutical chemist involving steps such as mixing, granulating and compressing, when necessary for tablet forms; or mixing, filling and dissolving the ingredients, as appropriate, to give the desired products for oral, parenteral, topical, intravaginal, intranasal, intrabronchial, intraoccular, intraaural and rectal administration.

The composition of the invention may further comprise one or more other compounds which are antitumor agents, such as a mitotic innibitors (e.g., vinblastine), alkylating agents (e.g., cisplatin, carboplatin and cyclophosphamide), dihydrofolate reductase inhibitors (e.g., methotrexate, piritrexim and trimetrexate), other thymidylate synthase inhibitors, antimetabolites (e.g., 5-fluorouracil and cytosine arabinoside), intercalating antibiotics (e.g., adriamycin and bleomycin), enzymes (e.g., asparaginase), topoisomerase inhibitors (e.g., etoposide) or biological response modifiers (e.g., interferon).

The composition of the invention may also comprise one or more other compounds, including antibacterial, antifungal, antiparasitic, antiviral, antipsoriatic and anticoccidial agents. Exemplary antibacterial agents include, for example, sulfonamide such as sulfamethoxazole, sulfadiazine, sulfameter or sulfadoxirie; dihydrofolate reductase inhibitors such as trimethoprim, bromodiaprim or trimetrexate; penicillins; cephalosporins; aminoglycosides; bacteriostatic inhibitors of protein synthesis; the quinolonecarboxylic acids and their fused isothiazolo analogs.

Another aspect of the invention relates to a therapeutic process of inhibiting the growth and proliferation of cells of higher organisms and microorganisms, which process comprises administering to a host, such as a vertebrate host (e.g., a mammal or bird) an effective amount of a compound according to the present invention. A particularly preferred therapeutic process comprises administering to a host an effective amount of a compound according to the present invention to inhibit the enzyme thymidylate synthase, The compounds of the invention are particularly useful in the treatment of mammalian hosts, such as human hosts, and in the treatment of avian hosts.

Any of the antiproliferative compounds described above, or pharmaceutically acceptable salts thereof, may be employed in the therapeutic process of the invention. The compounds of the invention may be administered in the form of a pharmaceutically acceptable composition comprising a diluent or carrier, such as those described above. Doses of the compounds preferably include pharmaceutical dosage units comprising an efficacious quantity of active compound. By an efficacious quantity is meant a quantity sufficient to inhibit the folate metabolic pathways and derive the beneficial effects therefrom through administration of one or more of the pharmaceutical dosage units. An exemplary daily dosage unit for a vertebrate host comprises an amount of up to about 1 gram of active compound per kilogram of the host, preferably one half of a gram, more preferably 100 milligrams, and most preferably about 50 milligrams per kilogram of the host.

The selected dose may be administered to a warmblooded animal or mammal, for example a human patient, in need of treatment mediated by folate metabolic pathways inhibition by any known method of administration, including topically (e.g. as an ointment or cream), orally, rectally (e.g., as a suppository), parentally, by injection or continuously by infusion, intravaginally, intranasally, intrabronchially, intraaurally or intraocularly.

The compounds according to the present invention may be characterized as producing any one or more of an antiproliferative effect, an antibacterial effect, an antiparasitic effect, an antiviral effect, an antipsoriatic effect, an antiprotozoal effect, an anticoccidial effect or an antifungal effect. The compounds are especially useful in producing an antitumor effect a vertebrate host harboring a tumor.

EXAMPLES

As stated previously, Table 1 discloses a number of preferred compounds according to the present invention. Examples of the process used to make several of these preferred compounds is set forth below.

The structures of all compounds of the invention were confirmed by proton magnetic resonance spectroscopy, infrared spectroscopy, elemental microanalysis and/or mass spectrometry. Infrared absorption spectra were taken on a Midac FT or a Perkin Elmer Model 457 spectrophotometer. Spectra were obtained as KBr (potassium bromide) pellets or neat films, and the peak values were reported in $cm^{-1}$.

Proton magnetic resonance spectra were determined using a General Electric QE-300 spectrometer operating at a field strength of 300 MHz. Chemical shifts are reported in parts per million (δ) by setting the references such that, in $CDCl_3$, the $CHCl_3$ peak is at 7.26 ppm and, in DMSO-$d_6$, the DMSO peak is at 2.49 ppm. Standard and peak multiplicities are designated as follows: s, singlet; d, doublet; dd, doublet of doublets; t, triplet; brs, broad singlet; brd, broad doublet; br, broad signal; m, multiplet.

Mass spectra were determined using a VG 7070E-HF high resolution mass spectrometer using the direct insertion method, an ionizing voltage of 70 eV, and an ion source temperature of 200° C. Elemental microanalysis provided results for the elements usually within ±0.4% of the theoretical values.

General Procedures

N-N-Dimethylformamide ("DMF") was dried over activated (250° C.) 3-Å molecular sieves; N,N-dimethylacetamide ("DMA") (Aldrich Gold Label grade) was similarly dried. Tetrahydrofuran ("THF") was distilled from sodium benzophenone ketyl under nitrogen. The term "ether" refers to diethyl ether.

Flash chromatography was performed using Silica gel 60 (Merck Art 9385). Where the crude solid was insoluble in the chosen eluant, it was dissolved in a more polar solvent, and Merck Art 7734 silica was added. The slurry was evaporated to dryness on a rotary evaporator fitted with a course glass frit to prevent spraying of the silica. The coated silica was then applied to the column. Thin layer chromatographs ("TLC") were performed on precoated sheets of silica 60 $F_{254}$ (Merck Art 5719). Extracts were dried over anhydrous $Na_2SO_4$ or $MgSO_4$. Melting points were determined on a Mel-Temp apparatus and were uncorrected.

Example 1

Preparation of Compounds 8A and 14A

Compounds 8A and 14A were prepared according to the following reaction scheme:

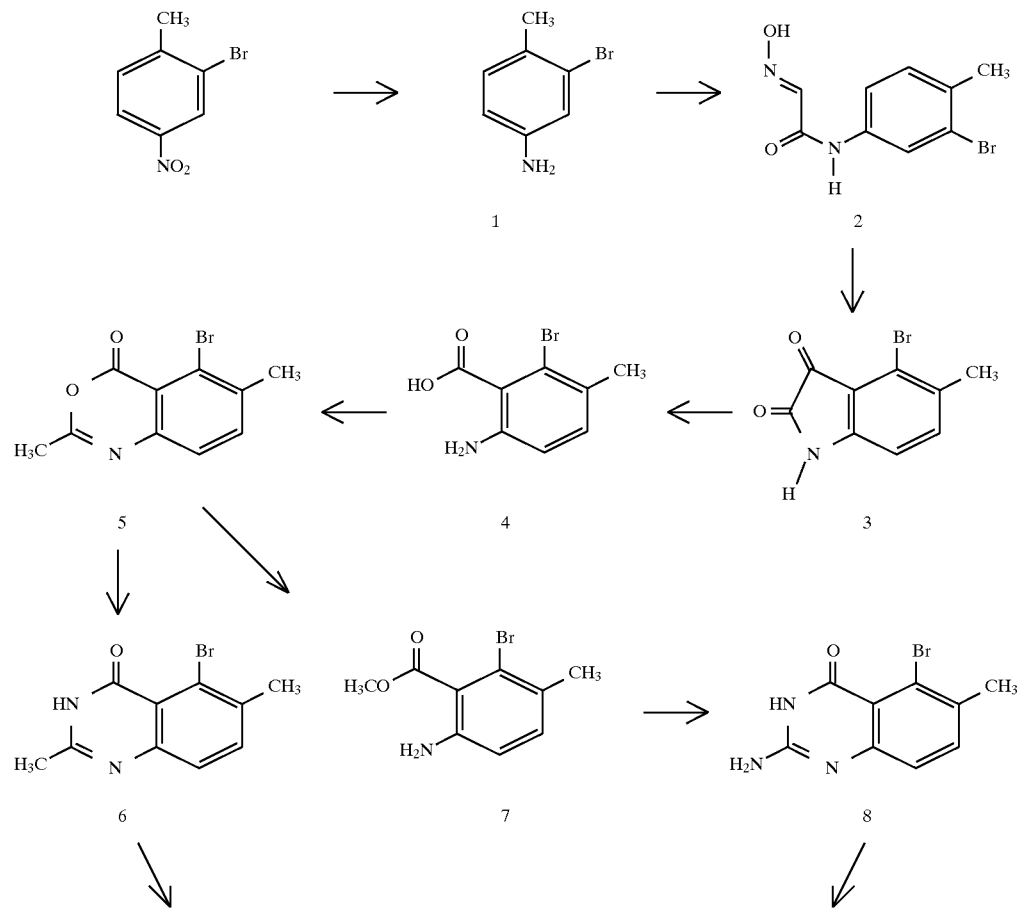

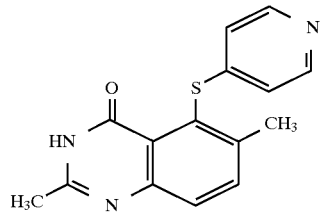

9
8A

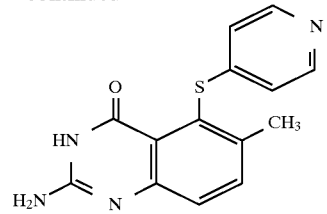

10
14A

Preparation of Intermediate Compound (1)—3-Bromo-4-methyl-aniline

A solution of 50.0 g (0.23 mol) 2-Bromo-4-nitro-toluene in 500 ml methanol was placed in a Parr hydrogenation bottle. To the solution was added 5.0 g Raney nickel. This mixture was hydrogenated at 30 psi $H_2$ on the Parr hydrogenator for three hours with agitation. The Parr bottle was vented, the reaction mixture was filtered through diatomaceous earth (celite), and the filtrate was evaporated to yield 41.0 g (95%) of a yellow oil. IR (neat) 3329, 3144, 2604, 1609, 1288, 1030, 812 cm$^{-1}$; $^1$H NMR (DMSO-d$_6$) δ 2.13 (s, 3H), 5.60 (bs, 2H), 6.46 (dd, 1H, J=8.1 Hz, 2.3 Hz), 6.79 (d, 1H, J=2.3 Hz), 6.94 (d, 1H, J=8.2 Hz). HRMS calcd. for $C_7H_8BrN$: 184.9843. Found: 184.9840.

Preparation of Intermediate Compound (2)—3-Bromo-4-methyl-α-isonitrosoacetanilide A mixture of 45.0 g chloral hydrate (0.27 mol), 65.0 g sodium sulfate (0.46 mol), 40.0 g 3-Bromo-4-methyl-aniline (1) (0.21 mol), 20 ml concentrated HCl, 55.0 g of hydroxylamine hydrochloride (0.79 mol) and 1.5 l of $H_2O$ were heated at 100° C. for one hour. The reaction mixture was cooled to 0° C., and the precipitate was collected by filtration. The solid was washed with $H_2O$ and dried to yield 41.0 g (76%) as a tan solid: M.P. 195°–197° C. IR (KBr) 3439, 3310, 3110, 2998, 2876, 2749, 1636, 1591, 1466, 1256, 905, 691 cm$^{-1}$; $^1$H NMR (DMSO-d$_6$) δ 2.28 (s, 3H), 3.50 (bs, 1H), 7.28 (d, 1H, J=8.3 Hz), 7.53 (dd, 1H, J=8.2, 2.1 Hz), 8.02 (d, 1H, J=2.0 Hz), 10.26 (s, 1H), 12.21 (s, 1H). Anal. Calcd. for $C_9H_9BrN_2O_2$: C, 42.04; H, 3.53; Br, 31.08; N, 10.90. Found: C, 42.71; H, 3.57; Br, 31.44; N, 11.09.

Preparation of Intermediate Compound (3)—4-Bromo-5-methylisatin

To 160 ml concentrated sulfuric acid at 80° C. was added 40 g (0.156 mol) of (2) and stirred for one hour. The reaction mixture was cooled to room temperature and then poured onto 2 l of crushed ice. The precipitate was filtered, washed with water and then washed with benzene. The red solid was added to 800 ml of boiling ethanol. The solution was allowed to cool to room temperature, collected and then washed with cold ethanol. 6-Bromo-5-methylisatin, as well as some of the desired product remains in the mother liquor, and can be separated by silica gel flash column chromatography. The filter cake was dried to yield 19 g (50.7%) of a red solid: M.P. 245°–248° C. IR (KBr) 3302, 1750, 1609, 1466, 1273, 675 cm$^{-1}$; $^1$H NMR (CDCl$_3$) δ 2.26 (s, 3H), 6.8 (d, 1H, J=7.9 Hz), 7.5 (d, 1H, J=8.3 Hz), 11.06 (s, 1H). Anala Calcd. for $C_9H_6BrNO_2$: C, 45.02; H, 2.52; Br, 33.28; N, 5.86. Found: C, 45.10; H, 2.54; Br, 33.19; N, 5.84.

Preparation of Intermediate Compound (4)—5-Methyl-6-bromo-anthranilic acid

A mixture of 80 ml 3N NaOH and 19 g of isatin (3) (0.08 mol) were heated at 80° C. To the solution was added 18 ml 30% $H_2O_2$, and the mixture was stirred for one hour. The mixture was cooled to 5° C. and acidified to pH5 with concentrated hydrochloric acid. The solution was evaporated to dryness and then added to 300 ml methanol. The mixture was filtered, and the filtrate was evaporated to yield 18 g of a tan solid (97.8% theory): M.P. (hydrochloride) 290°–294° C. IR (KBr) 3619, 3229, 1578, 1478, 1412, 1381, 1084, 1010, 820, 706 cm$^{-1}$; $^1$H NMR (DMSO-d$_6$) δ 2.13 (s, 3H), 4.9 (s, 2H), 6.4 (d, 1H, J=7.9 Hz), 6.74 (d, 1H, J=7.8 Hz).

Preparation of Intermediate Compound (5)—5-Bromo-6-methyl acetylanthranil (5-bromo-2,6-dimethyl-4H-3,1-benzoxazin-4-one)

A mixture of 18 g anthranilic acid (4) (0.078 mol) in 300 ml acetic anhydride was heated at reflux for 3 hours. The solution was cooled to 0° C. and filtered. The filter cake was wished with acetone to yield 16 g (81% theory) as a white solid (M.P. 190°–194° C.) which was used without further purification. IR (KBr) 3460, 1750, 1660, 1574, 1416, 1260, 1070, 841 cm$^{-1}$; $^1$H NMR (CDCl$_3$) δ 2.45 (s, 3H), 2.55 (s, 3H), 7.40 (d, 1H, J=8.2 Hz), 7.64 (d, 1H, J=8.0 Hz). HRMS calcd. for $C_{10}H_8BrNO_2$: 252.9738. Found: 252.9743.

Preparation of Intermediate Compound (6)—5-Bromo-3,4-dihydro-2,6-dimethylquinazolin-4-one Anhydrous ammonia (50 ml) was condensed into a flask containing 8.5 g (34.0 mmol) anthranil (5), and the reaction was stirred for 3 hrs. The solvent was evaporated to give a residue, and 75 ml of 1N NaOH was added. The reaction mixture was heated at reflux temperature for 1 hr. The resulting solution was cooled to 0° C. and acidified to pH4 with concentrated hydrochloric acid. The mixture was filtered, and the filter cake was washed with water and then dried to yield 7.1 g (82.5% theory) of 6 as a tan solid: M.P. 288°–291° C. (dec.) The product was used without further purification. IR (KBr) 2910, 2620, 1680, 1630, 1460, 1377, 1298, 1128, 872 cm$^{-1}$; $^1$H NMR (DMSO-d$_6$) δ 2.33 (s, 3H), 2.43 (s, 3H), 7.49 (d, 1H, J=8.3 Hz), 7.70 (d, 1H, J=8.3 Hz), 12.20 (bs, 1H). HRMS calcd. for $C_{10}H_9BrN_2O$: 251.9898. Found: 251.9908.

Preparation of Compound (7)—Methyl-2-amino-6-bromo-5-methylbenzoate

A mixture of 10 g (0.039 mol) anthranil (5) in 75 ml methanol was heated at reflux for 2 hrs. To the solution was added 10 ml concentrated hydrochloric acid, and the mix was heated for an additional two hours. The reaction mixture was evaporated to dryness. The residue was dissolved in 20 ml $H_2O$ and neutralized to pH7 with triethylamine. The aqueous solution was extracted with methylene chloride. The layers were separated, and the organic layer was dried over magnesium sulfate, filtered and evaporated to dryness to yield 6.0 g of (7), as an orange oil (63% theory). IR (neat) 3483, 3410, 3220, 3000, 2950, 2851, 1720, 1620, 1560, 1430, 1288, 1120, 1015, 816 cm$^{-1}$; $^1$H NMR (CDCl$_3$) δ 2.31 (s, 3H), 3.95 (s, 3H), 4.10 (bs, 2H), 6.60 (d, 1H, J=8.2 Hz), 7.05 (d, 1H, J=8.1 Hz). HRMS calcd. for C$_9$H$_{10}$BrNO$_2$: 242.9890. Found: 242.9895.

Preparation of Intermediate Compound (8)—2-Amino-5-bromo-3,4-di-hydro-6-methylquinazolin-4-one To a solution of methyl ester (7) (6 g, 24 mmol) in 50 ml of diglyme was added 3 g (24 mmol) of chloroformamidine hydrochloride. The mixture was heated at reflux for 1 hr. The mixture was cooled to 0° C. and filtered. The solid was washed with ether and then dried to yield 6.25 g (88% theory) of a tan solid: M.P. (hydrochloride) >390° C. The product was used without further purification. IR (KBr) 3140, 2950, 1670, 1620, 1471, 1402, 816, 600 cm$^{-1}$; $^1$H NMR (DMSO-d6) δ 2.28 (s, 3H), 6.75 (bs, 2H), 7.0 (d, 1H, J=8.3 Hz), 7.40 (d, 1H, J=8.0 Hz), 11.8 (bs, 1H). HRMS calcd. for C$_9$H$_8$BrN$_3$O: 253.9927. Found: 253.9929.

Preparation of Compound (9) (Compound 8A)—3,4-Dihydro-2,6-dimethyl-4-oxo-5-(4-pyridylthio)-quinazoline To a solution of 3.2 g 4-mercaptopyridine (28.8 mmol) in 50 ml of anhydrous N,N-Dimethylacetamide at 0° C. was added 1.24 (28.8 mmol) NaH (60% dispersion in mineral oil), and the mix was stirred for 1 hr. To this reaction mixture was added 3.1 g bromoquinazoline (6) (0.012 mol), 1.4 g copper (I) bromide, and 0.70 g of copper (I) oxide. The mix was heated at 90° C. for 4 hrs. The reaction mixture was evaporated to dryness, 50 ml of an H$_2$S/methanol solution (10 g/l) was added to the residue, and the mixture was stirred for 1 hr. The mixture was filtered, and the filtrate was evaporated to dryness. The solid was purified via flash chromatography on silica gel using MeOH/CH$_2$Cl$_2$ (5:95) to yield 1.7 g (48% theory) of a tan solid: M.P. 235°–238° C.; IR (KBr) 3430, 1670, 1633, 1575, 1460, 1408, 1300, 841, 820, 714 cm$^{-1}$; $^1$H NMR (DMSO-d$_6$) δ 2.28 (s, 3H), 2.40 (s, 3H), 6.80 (d, 2H, J=5.9 Hz), 7.60 (d, 1H, J=8.3 Hz), 7.80 (d, 1H, J =8.5 Hz), 8.24 (d, 2H, J=6.5 Hz), 12.10 (bs, 1H). Anal. Calcd. for C$_{15}$H$_{13}$N$_3$OS H$_2$O C, 59.80; H, 4.98; N, 13.95; S, 10.63. Found: C, 59.58; H, 4.90; N, 13.89; S, 10.62. HRMS Calcd. for C$_{15}$H$_{13}$N$_3$OS: 283.0773. Found: 283.0779.

Preparation of Compound (10) (Compound 14A)—2-Amino-3,4-dihydro-6-methyl-4-oxo-5-(4-pyridylthio)-quinazoline To a solution of 17.2 g 4-mercaptopyridine (15.5 mol) in 250 ml of anhydrous N,N-Dimethylacetamide at 0° C. was added 6.2 g of (15.5 mol) NaH (60% dispersion in mineral oil), and the reaction was stirred for 1 hr. To the solution was added 15 g aminoquinazoline HCl (8) (51.3 mmol), 4.5 g copper (I) bromide, and 4.5 g copper (I) oxide. The mixture was heated at 90° C. for 4 hrs., and then concentrated under vacuum. To the resulting solid was added 150 ml H$_2$S/MeOH solution (20 g/l). The dark mixture was stirred for 1 hr., the precipitated CuS was removed by filtration, and the methanolic filtrate was evaporated. The solid was washed with methylene chloride, followed by ethyl ether and finally boiling isopropanol to yield 7.5 g (50% theory) of (10) as a tan solid: M.P. 301°–302° C.; IR (KBr) 3320, 3150, 2750, 1670, 1575, 1466, 1305, 1220, 804, 710 482 cm$^{-1}$; $^1$H NMR (DMSO-d$_6$) δ 2.30 (s, 3H), 6.35 (bs, 2H), 6.80 (d, 2H, J=5.9 Hz), 7.26 (d, 1H, J=8.4 Hz), 7.58 (d, 1H, J=8.5 Hz), 8.25 (bs, 2H), 10.85 (bs, 1H). Anal. Calcd. for C$_{14}$H$_{12}$N$_4$OS.1.5 H$_2$O: C, 54.00; H, 4.86; N, 18.00; S, 10.30. Found: C, 53.81; H, 4.25; N, 17.71; S, 10.28. HPMS calcd. for C$_{14}$H$_{12}$N$_4$OS: 284.0734. Found: 284.0732.

Example 2

Preparation of Compounds 13A and 15A

Compounds 13A and 15A were prepared according to the following reaction scheme:

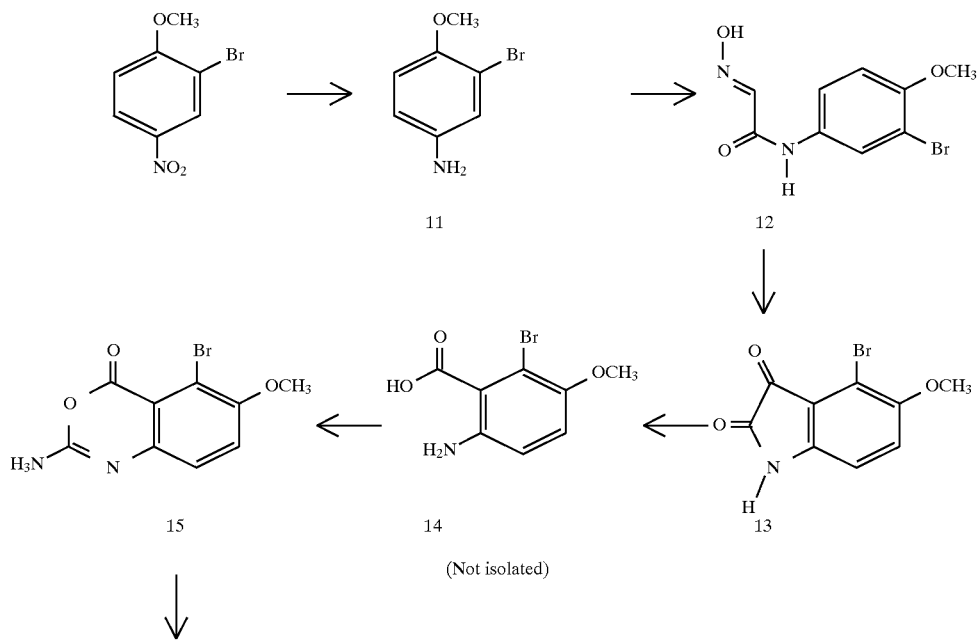

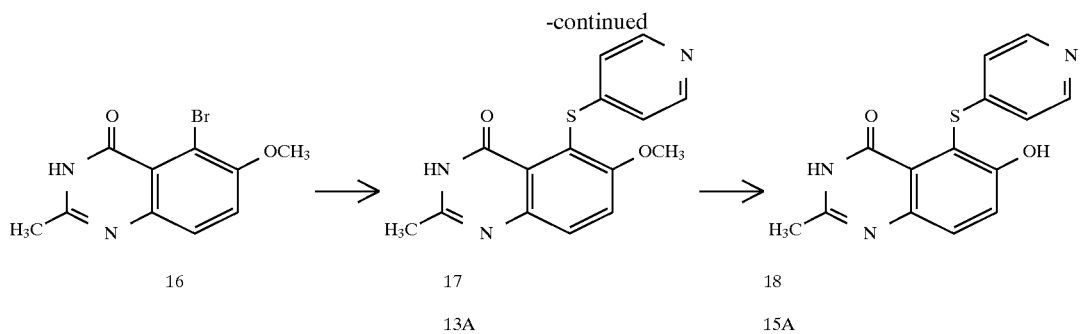

16 → 17 → 18

13A    15A

Preparation of Intermediate Compound (11)—3-Bromo-4-methoxyaniline

To a solution of 38.0 g of 1-bromo-4-nitroanisole (0.164 mol) in 300 ml of methanol/THF (1:1) was added 5 ml of anhydrous hydrazine and 4.0 g of activated Raney nickel catalyst suspended in ethanol. The mixture was stirred and heated to a gentle reflux, where upon the mixture began to effervesce. Within a period of 3 hrs., 7 additional ml of hydrazine and 4 additional grams of Raney nickel were introduced into the reaction. The warm reaction mixture was vacuum filtered through a pad of silica gel to remove the catalyst, and the pad was thoroughly washed with ethyl acetate. The filtrate was concentrated, and the dark brown oil was placed under high vacuum to remove traces of solvent. The product decomposes readily and was used as is. $^1$H NMR (CDCl$_3$) δ 3.46 (s, 2H), 6.60 (dd, 1H, J=8.6, 2.7 Hz), 6.73 (d, 1H, J=8.6 Hz), 6.92 (d, 1H, J=2.7 Hz).

Preparation of Intermediate Compound (12)—3-Bromo-4-methoxy-α-isonitrosoacetanilide In a 250 ml 3-neck round bottom flask, 84 ml water was added to 6.3 g (37.8 mmol) chloralhydrate. The flask was fitted with a mechanical stirrer and reflux condenser, and 90 g anhydrous sodium sulfate powder was added over a period of 1 minute with constant stirring. A solution of 6.3 g (31.2 mmol) of aniline (11) in 3.0 ml conc. HCl and 21 ml water was added, followed by a solution of 7.7 g (112 mmol H$_2$NOH.HCl in 35 ml water. The mixture was slowly heated to reflux with constant stirring and continued for 2 minutes at which time brown crystals formed. The mixture was cooled, the solid filtered off, washed well with water and dried to constant weight by vacuum. The resulting solid weighed 5.65 g (66% theoretical) and was pure enough for the next step. An analytical sample was prepared by recrystallization. M.P. 202°–203° C. (hexane, EtOAc). IR (KBr) 3409, 2875, 2056, 2023, 1643, 1634, 1543, 1502, 1295, 1270, 1047, 799 cm$^{-1}$; $^1$H NMR (CDCl$_3$, one drop DMSO-d$_6$) δ 6 3.88 (s, 3H), 6.87 (d, 1H, J=8.9 Hz), 7.53 (m, 2H), 7.83 (d, 1H, J=2.5 Hz), 8.49 (s, 1H), 11.60 (s, 1H, NH). Anal. Calcd. for C$_9$H$_9$BrN$_2$O$_3$.0.11 EtOAc: C, 40.09; H, 3.52; Br, 28.26; N, 9.91. Found: C, 40.45; H, 3.44; Br, 27.86; N, 10.34.

Preparation of Intermediate Compound (13)—4-Bromo-5-methoxyisatin

Vacuum dried α-Isonitrosoacetanilide (12) (3.0 g; 11 mmol) was slowly added to 8 ml conc. H$_2$SO$_4$ at 50° C. while being stirred. The reaction mixture first became yellow, and then turned dark. The temperature was raised to 65° C. for 10 minutes, and the reaction was followed by TLC (EtOAc/hexane; 40:60). Heating at 65°–70° C. was resumed until all the starting material was consumed as judged by TLC. Upon completion, the reaction mixture was cooled and added to 80 g of crushed ice with stirring. A dark red a solid formed and was filtered off, washed free of acid by water and dried under vacuum. The resulting substance was purified by chromatography on a flash silica column using a gradient system of EtOAc/hexane; 40:60; 50:50; 60:40; 70:30; 80:20. The undesired isomer, 6-Bromo-5-methoxyisatin eluted first, followed by the desired isomer (13), which was isolated as a red solid (0.71 g; 25% yield). M.P. 250°–251° C. IR (KBr) 2064, 1758, 1750, 1634, 1278 cm$^{-1}$; $^1$H NMR (CDCl$_3$, one drop DMSO-d$_6$) δ 3.91 (s, 3H), 6.84 (d, 1H, J=8.8 Hz), 7.09 (d, 1H, J=8.8 Hz), 10.88 (s, 1H). Anal. Calcd. for C$_9$H$_6$BrNO$_3$: C, 42.19; H, 2.34; Br, 31.25; N, 5.47. Found: C, 42.27; H, 2.37; Br, 31.30; N, 5.42.

Preparation of Intermediate Compound (15)—5-Bromo-6-methoxyacetylanthranil(5-bromo-2,6-dimethyl-4H-3,1-benzoxazin-4-one)

A magnetically stirred solution of 2.28 g (8.9 mmol) isatin (13), in 13.4 ml of 2N aq. NaOH (26.7 mmol) was cooled to 0° C. To this cold solution 0.90 ml of 30% H$_2$O$_2$ (8.9 mmol) was added gradually keeping the temperature below 20° C. The progress of the reaction was followed by TLC (EtOAc/hexane; 40:60). An additional 0.20 ml of 30% H$_2$O$_2$ was added, and the reaction mixture was stirred 20 minutes at room temperature. At this time, TLC indicated consumption of the starting material. The mixture was acidified with glacial acetic acid to pH4 and concentrated via a cryogenic trap at −78° C., leaving crude 6-Bromo-5-methoxyanthranilic acid (14), as a grey semi-solid. This slurry was treated with 28 ml of acetic anhydride and refluxed for 40 minutes. The dark mixture was then concentrated as before. To the residue was added an excess of ethyl acetate:hexane (2:1). The mixture was heated and filtered hot through silica gel to remove insoluble and colored particulants. The solution was partially concentrated and allowed to cool, and the product crystallized yielding 1.71 g (71% based on starting isatin (13)). M.P. 228°–229° C. (dec.). IR (KBr) 3397, 2039, 1717, 1651, 1625, 1543, 1295, 1055, 881, 617 cm$^{-1}$; $^1$H NMR (CDCl$_3$) δ 2.42 (s, 3H), 3.98 (s, 3H), 7.34 (d, 1H, J=8.9 Hz), 7.51 (d, 1H, J=8.9 Hz), Anal. Calcd. for C$_{10}$H$_8$BrNO$_3$: C, 44.44; H, 2.96; Br, 29.62; N, 5.19. Found: C, 44.32; H, 3.04; Br, 29.53; N, 5.09.

Preparation of Intermediate Compound (16)—5-Bromo-3,4-dihydro-6-methoxy-2-methyl-quinazolin-4-one To 1.25 g (4.6 mmol) of the anthranil (15), in a dried round bottom flask equipped with a dry ice condenser, was condensed approximately 50 ml of anhydrous NH$_3$. The mixture was magnetically stirred for 40 min. At this time, the dry ice condenser was removed, and the NH$_3$ was allowed to evaporate. Upon evaporation, 15 ml water and 1.5 ml of 2N NaOH were added, and the solution was refluxed for 1 hr. The solution was then cooled to room temperature, and 1N HCl was added adjusting the pH to approximately 9 and thus precipitating the quinazoline. The white substance was filtered off, washed with water and dried, yielding 0.71 g (57%). M.P. 273°–274° C. IR (KEr) 3189, 3074, 2990, 2974, 2899, 2362, 1676, 1643, 1552, 1461, 1303, 1286, 1063, 872, 832 cm$^{-1}$; $^1$H NMR (CDCl$_3$) δ 2.39 (s, 3H), 3.98 (s, 3H), 7.39 (d, 1H, J=9.0 Hz), 7.59 (d, 1H, J=9.0 Hz), 11.60 (s, 1H), Anal. Calcd. for C$_{10}$H$_9$BrN$_2$O$_2$: C, 44.61; H, 3.35; Br, 29.74; N, 10.41; Found: C, 44.56; H, 3.40; Br, 29.63; N, 10.36.

Preparation of Intermediate Compound (17) (Compound 13A)—3,4-Dihydro-6-methoxy-2-methyl-4-oxo-5-(4-pyridylthio)-quinazoline To 78 mg (0.7 mmol) of 4-Mercaptopyridine was added 34 mg (0.5 mmol) of solid NaOH in 1 ml of dry DNA. To the resulting solution, 134 mg (0.5 mmol) of quinazolinone (16) dissolved in 2 ml dry DMA was added. The mixture was kept under N$_2$, and a finely ground catalyst mixture containing 44 mg CuBr and 22 mg Cu$_2$O was added. The mixture was stirred magnetically and heated to 135° C., until the reaction was complete as judged by TLC (anh. NH$_3$/MeOH/CHCl$_3$; 0.5:4.5:9.5). The solvent was removed under high vacuum through a cryogenic trap cooled to −78° C. The desired product was isolated by flash chromatography (anh. NH$_3$/MeOH/CHCl$_3$; 0.5:4.5:9.5) on silica, yielding 130 mg (89%) of (17) as a white powder. M.P. 248°–249° C. (dec.). IR (KBr) 3358, 3073, 2933, 1682, 1634, 1574, 1475, 1462, 1318, 1277, 1059, 835, 710 cm$^{-1}$; $^1$H NMR (CDCl$_3$) δ 2.36 (s, 3H), 3.84 (s, 3H), 6.90 (d, 2H, J=5.1 Hz), 7.48 (d, 1H, J=9.1 Hz), 7.79 (d, 1H, J=9.1 Hz), 8.28 (d, 2H, J=5.1 Hz), 10.86 (s, 1H). Anal. Calcd. for C$_{15}$H$_{13}$N$_3$O$_2$S: C, 60.18; H, 4.38; N, 14.04; S, 10.71. Found: C, 60.28; H, 4.43; N, 14.07; S, 10.63. HRMS Calcd. for C$_{15}$H$_{13}$N$_3$O$_2$S: 299.0730. Found: 299.0718.

Preparation of Intermediate Compound (18) (Compound 15A)—3,4-Dihydro-6-hydroxy-2-methyl-4-oxo-5-(4-pyridylthio)-quinazoline To cleave the methyl ether, quinazoline (17) (100 mg; 0.30 mmol) was gently refluxed with 2 ml of a 1:1 mixture of 48% aq. HBr and glacial AcOH for 8 hrs. At this time, the solvent was removed via high vacuum through a cryogenic trap at −78° C. The obtained residue was dissolved in 10% anh. NH$_3$ in MeOH, and subjected to flash column chromatography on silica (anh. NH$_3$/MeOH/CHCL$_3$; 0.5:4.5:9.5) yielding 62 mg of (18) as a white powder (65%) M.P. 246°–247° (dec). IR (KBr) 3450, 3240, 3073, 1667, 1634, 1580, 1464, 629 cm$^{-1}$; $^1$H NMR (CDCl$_3$) δ 2.40 (s, 3H), 6.83 (d, 2H, J=6.0 Hz), 7.40 (d, 1H, J=9.0 Hz), 7.59 (d, 1H, J=9.0 Hz), 8.20 (d, 2H, J=6.0 Hz), 8.51 (s, 1H), 11.51 (s, 1H). Anal. Calcd. for C$_{14}$H$_{11}$N$_3$O$_2$S: C, 58.94; H, 3.13; N, 11.97; S, 11.22. Found: C, 58.98; H, 3.16; N, 12.00; S, 11.61. HRMS calcd. for C$_{14}$H$_{11}$N$_3$O$_2$S: 285.05733. Found: 285.05720.

Example 3

Preparation of Compound 12A

Compound 12A was prepared according to the following reaction scheme:

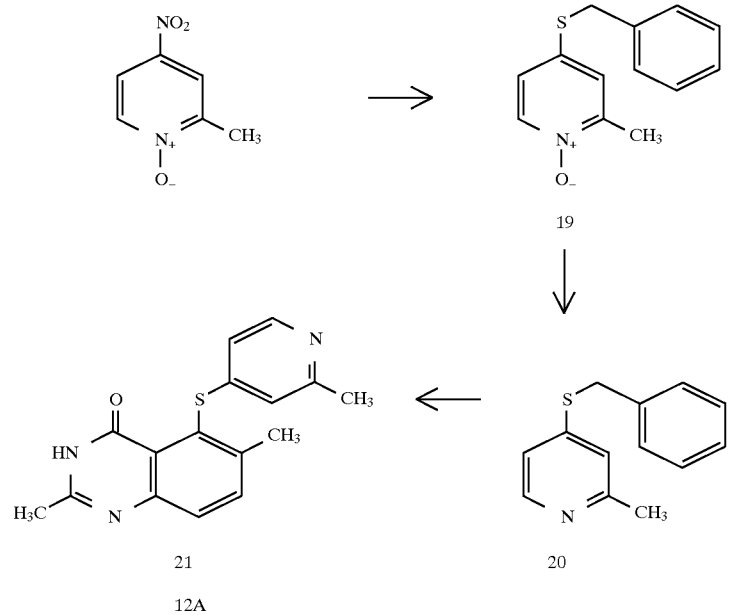

Preparation of Compound (19)—4-Benzylthio-2-picoline-N-oxide

Mineral oil was removed from potassium hydride (0.11M; 35 wt. % dispersion in mineral oil) by several washings with petroleum ether (5×50 ml). The remaining petroleum ether was removed under vacuum. To this dry solid, 350 ml of anhydrous THF was added cautiously. The well stirred suspension was cooled to 0° C. To this mixture, 14.1 ml (0.12 mol) of benzylmercaptan was added dropwise over a period of 30 minutes. The resultant milky white mixture was warmed to room temperature and allowed to stir for an additional 30 minutes. The mixture was then cooled to−30°

C., and 15.41 g (0.1 mol) of 4-nitro-2-picoline-N-oxide was added portionwise. The mixture became dark orange-brown in color. Once warmed to room temperature, the mixture was refluxed for one hour. At this time, the reaction was cooled to 0° C. and quenched with 50 ml of water. The pH of the mixture was adjusted to approximately 6 with 2M HCl, and extracted with dichloromethane (3×300 ml). The combined organic layers were dried (anhydrous $Na_2SO_4$), and the solvent was removed under reduced pressure. The crude residue was chromatographed on flash silica gel with MeOH/$CH_2Cl_2$ (Gradient: 3:97, 4:96, 5:95). The pure product was isolated (6.94 g; 30% yield) as a tan solid: M.P. 98°–99° C.; IR (KBr) 3063, 3028, 1612, 1466, 1236, 831, 715, 675 cm$^{-1}$; $^1$H NMR (CDCl$_3$) δ 2.45 (s, 3H), 4.16 (s, 2H), 6.97 (dd, 1H, J=6.8, 2.7 Hz), 7.07 (d, 1H, J=2.7 Hz), 7.32 (m, 5H), 8.09 (d, 1H, J=6.8 Hz). Anal. Calcd. for $C_{13}H_{13}NOS$: C, 67.50; H, 5.66; N, 6.05; S. 13.86. Found: C, 67.51; H, 5.69; N, 6.08; S, 13.77.

Preparation of Intermediate Compound (20)—4-Benzylthio-2-picoline

Compound (19), (1.97 g, 8.5 mmol) was dissolved into 50 ml of chloroform. The solution was stirred, cooled to 0° C., and 1.75 ml (17.4 mmol) of phosphorous trichloride was added dropwise. Once the addition was complete, the reaction mixture was brought to room temperature and then heated slightly under reflux temperature (approximately 55° C.) until no starting N-oxide was present by TLC (MeOH/$CH_2Cl_2$; 5:95). The solution was then recooled to 0° C., and 10 gm of ice was added with vigorous stirring. The mixture was made basic (pH 8) by careful addition of 1M NaOH, and the organic phase was separated. The agueous layer was extracted with dichloromethane (3×50 ml), and the organic layers were combined and dried (anhydrous $Na_2SO_4$). Removal of the solvent under reduced pressure gave an oil which was chromatographed on a short flash silica column using MeOH/$CH_2Cl_2$; 3:97. The product was isolated as a white solid (1.54 g; 84% yield): M.P. 69°–70° C.; IR (KBr) 3028, 3003, 2920, 1583, 1454, 864, 815, 719, 702 cm$^{-1}$; $^1$H NMR (CDCl$_3$) δ 2.55 (s, 3H), 4.22 (s, 2H), 7.03 (m, 2H), 7.35 (m, 5H), 8.28 (d, 1H, J=5.5 Hz). Anal. Calcd. for $C_{13}H_{13}NS$: C, 72.52; H, 6.08; N, 6.50; S, 14.90. Found: C, 72.46; H, 6.11; N, 6.50; S, 14.80.

Preparation of Compound (21) (Compound 12A)—3,4-Dihydro-2,6-dimethyl-4-oxo-5-[4-(2-picolinylthio)]-quinazoline To a solution of 5 ml $NH_3$ condensed into 5 ml THF kept at −78° C. was added 115 mg sodium metal (5.0 mmol). The deep blue solution was stirred for 15 minutes. To the reaction mixture was added 1.0 g (4.65 mmol) of 4-benzylthio-2-picoline (20), and the reaction was stirred for 1½ hrs. at 0° C. The solvent was removed under vacuum, and to the resulting solid was added 10 ml of anhydrous N,N-Dimethylacetamide, 0.5 g quinazoline (6) (2.0 mmol) and 0.25 g of copper (I) bromide. The mix was heated at 90° C. for 4 hrs. The solvent was removed under vacuum, and the solid was treated with 10 ml of $H_2S$/MeOH solution (20 g/l). The insoluble CuS was filtered off, and the filtrate was evaporated to dryness. The solid was purified using flash chromatography on silica with MeOH/$CH_2Cl$ (5:95) to yield 400 mg (84% theory) of a tan solid: M.P. 225°–227° C.; IR (KBr) 3480, 3160, 3053, 2960, 1670 1630, 1590, 1460, 1298, 831 cm$^{-1}$; $^1$H NMR (DMSO-d$_6$) δ 2.28 (s, 6H), 2.36 (s, 3H), 6.60 (bs, 1H), 6.80 (6s, 1H), 7.60 (d, 1H, J=8.4 Hz), 7.80 (d, 1H, J=8.4 Hz). Anal. Calcd. for $C_{16}H_{15}N_3OS.0.5$ $H_2$: C, 62.73; H, 5.22; N, 13.72; S, 10.46. Found: C, 63.08; H, 5,20; N, 13.73; S, 10.50. HPMS Calcd. for $C_{16}H_{15}N_3OS$: 297.0936. Found: 297.0936.

Example 4

Preparation of Compound 16A

Compound 16A was prepared according to the following reaction scheme:

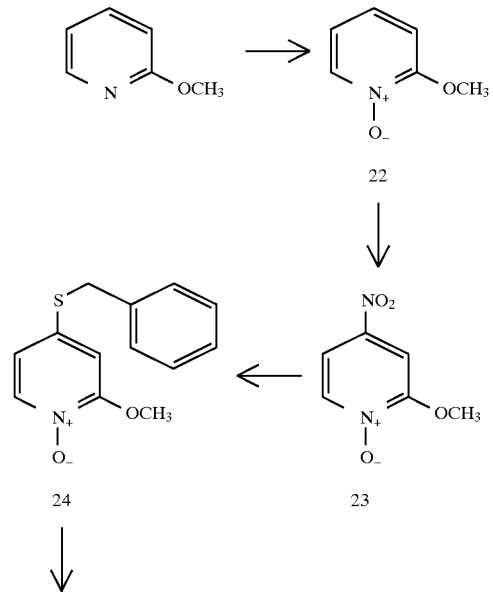

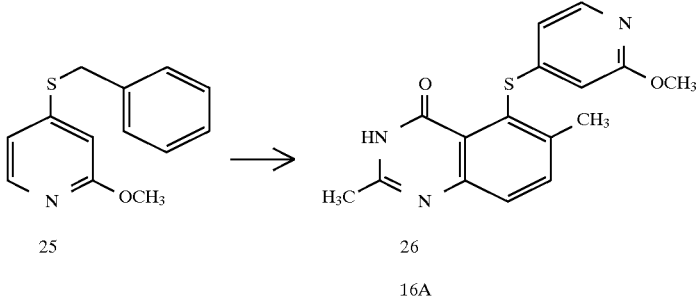

25 → 26

16A

Preparation of Intermediate Compound (22)—2-Methoxypyridine-N-oxide

This compound, originally prepared by H. J. Den Hertog and M. Van Ammers, *Rec. Trav. Chim.* 1955, 74, 1160, was synthesized using a different procedure. To a solution of 21.83 of 2-methoxypyridine (0.2 mol) in glacial acetic acid (80 ml), was cautiously added 30% hydrogen peroxide (20 ml). The stirred mixture was heated to 80° C. for 3 hrs, and cooled to room temperature. An additional 20 ml of 30% $H_2O_2$ was added, and the clear solution was heated at 80° C. for 12 hrs. The solution was concentrated to half the original volume under vacuum, and 100 ml of water was added. The solution was reconcentrated, and the process was repeated two times (2×100 ml $H_2O$). The syrup was placed under vacuum to remove remaining water and acetic acid. After time, a white solid formed. The material obtained in quantitative yield was used without further purification; M.P. 128°–130° C.; IR (KBr) 3447, 1613, 1570, 1508 1447, 1316, 1214, 1015, 764 cm$^{-1}$; $^1$H NMR (CDCl$_3$) δ 4.05 (s, 3H), 6.91 (d, 1H, J=8.0 Hz), 6.92 (m, 1H), 7.33 (dt, 2H, J=8.0, 1.6 Hz), 8.3 (dd, 1H, J=6.3, 1.6 Hz). HRMS Calcd. for $C_6H_7NO_2$: 125.0477. Found: 125.0474.

Preparation of Intermediate Compound (23)—2-Methoxy-4-nitropyridine-N-oxide

The nitration was carried out using the method of Den Hertog and Van Ammers[3]. The results obtained from this experiment differ from those reported. Concentrated $H_2SO_4$ (35 ml) was cooled to 0° C., and 15.3 g of N-oxide (22) (0.12 ml) was cautiously added in portions. To this stirred solution, kept at 0° C., was added the nitrating mixture (conc . $H_2SO_4$; 35 ml: fuming $HNO_3$; 60 ml) dropwise. The ice bath was removed, and the mixture was heated to 75° C. for 90 mins. The mixture was recooled to 0° C. and cautiously, poured onto 150 g of ice. With vigorous stirring, portions of solid $K_2CO_3$ were added until the pH was 7. The liquid was then extracted several times with $CH_2Cl_2$ (3×200 ml). The aqueous layer was continuously extracted with $CHCl_3$. The organic layers were combined, dried over anhydrous $Na_2SO_4$ and concentrated to give a yellow solid. The solid was chromatographed on a flash silica column using a gradient system of MeOH/$CH_2Cl_2$; 2:98, 3:97; 4:96; 5:95. A mixture of 2-methoxy-4-nitropyridine and 2-methoxy-5-nitropyridine (2.9 g) eluted first, followed by 2-methoxy-4-nitropyridine-N-oxide (6.4 g), and then 2-methoxy-5-nitropyridine-N-oxide (2.9 g). Compound (23), was obtained as a yellow solid (30%): M.P. 176°–178° C. (decomp.); (Literature: 154.5°–158.5° C., dec.)2; IR (KBr) 3106, 3082, 1601, 1528, 1346, 1296, 1231, 1088, 1011, 660 cm$^{-1}$; $^1$H NMR (CDCl$_3$) δ 4.18 (s, 3H), 7.73 (d, 1H, J=2.9 Hz), 7.78 (dd, 1H, J=7.1, 2.9 Hz), 8.35 (d, 1H, J=7.1 Hz). Anal. Calcd. for $C_6H_6N_2O_4$: C, 42.36; H, 3.56; N, 16.47. Found: C, 42.42; H, 3.57; N, 16.41.

Preparation of Intermediate Compound (24)—4-Benzylthio-2-methoxypyridine-N-oxide The pyridine-N-oxide (24) was prepared in similar fashion to the preparation of compound (19), with the following changes. Once the 4-nitro-2-methoxypyridine-N-oxide was added, the reaction mixture was allowed to warm to room temperature. Stirring was continued for 12 hrs. The precipitated solid that forms was filtered and washed with ice cold THF. The solid was dried under vacuum and shown to be one spot by TLC (MeOH/$CH_2Cl_2$; 10:90). The filtrate was concentrated and flash chromatographed on silica with MeOH/$CH_2Cl_2$ (gradient: 4:96, 5:95 6:94). An analytically pure tan solid was isolated. The total combined yield was 70%. M.P. 131°–133° C.; IR (KBr) 3105, 3038, 3005, 1670, 1610, 1543, 1483, 1290, 1211, 1132, 1016, 802 cm$^{-1}$; $^1$H NMR (CDCl$_3$) δ 3.95 (s, 3H), 4.19 (s, 2) 6.64 (d, 1H, J=2.4 Hz), 6.78 (dd, 1H, J=6.9, 2.4 Hz), 7.33 (m, 5H), 8.09 (d, 1H, J=6.9 Hz). Anal. Calcd. for $C_{13}H_{13}NO_2S$: C, 63.13; H, 5.30; N, 5.66; S, 12.96. Found: C, 62.88; H, 5.28; N, 5.62; S, 12.89.

Preparation of Intermediate Compound (25)—4-Benzylthio-2-methoxypyridine

The starting pyridine-N-oxide (24), (1.85 g) was reduced using the method to prepare compound (20), except heating of the mixture was not necessary. The reaction was complete in approximately 90 minutes. Flash silica chromatography using ether/petroleum ether, 5:95; yielded 1.57 g (90%) of compound (25) as a tan solid. M.P. 35°–36° C.; IR (KBr) 3028, 2943, 1589, 1543, 1385, 1307, 1037, 715 cm$^{-1}$; $^1$H NMR (CDCl$_3$) δ 3.98 (s, 3H), 4.23 (s, 2H), 6.64 (d, 1H, J=1.6 Hz), 6.84 (dd, 1H, J=5.9, 1.6 Hz), 7.35 (m, 5H), 7.98 (d, 1H, J=5.9 Hz). Anal Calcd. for $C_{13}H_{13}NOS$: C, 67.50; H, 5.66; N, 6.05; S, 13.86. Found: C, 67.60; H, 5.70; N, 6.10; S, 13.80.

Preparation of Compound (26) (Compound 16A)—3,4-Dihydro-2,6-dimethyl-4-oxo-5-[4-(6-methoxypyridylthio)]quinazoline This compound was prepared in 6–7% yield as described for (21) (Compound 12A). Tan solid; M.P. 223°–226° C.; IR (KBr) 3445, 1684, 1675, 1669, 1452, 1394, 1320, 1038 cm$^{-1}$; $^1$H NMR (DMSO-d$_6$) δ 2.28 (s, 3H), 2.35 (s, 3H), 3.70 (s, 3H), 6.05 (s, 1H), 6.49 (dd, 1H, J=4.1, 2.9 Hz), 7.60 (d, 1H, J=8.5 Hz), 7.78 (d, 1H, J=8.4 Hz), 7.85 (d, 1H, J=5.4 Hz), 12.10 (s., 1H). HRMS calcd. for $C_{16}H_{15}N_3O_3S$: 313.0885. Found: 313.0882.

Example 5

Preparation of Compounds 17A and 18A

Compounds 17A and 18A were prepared according to the following reaction scheme:

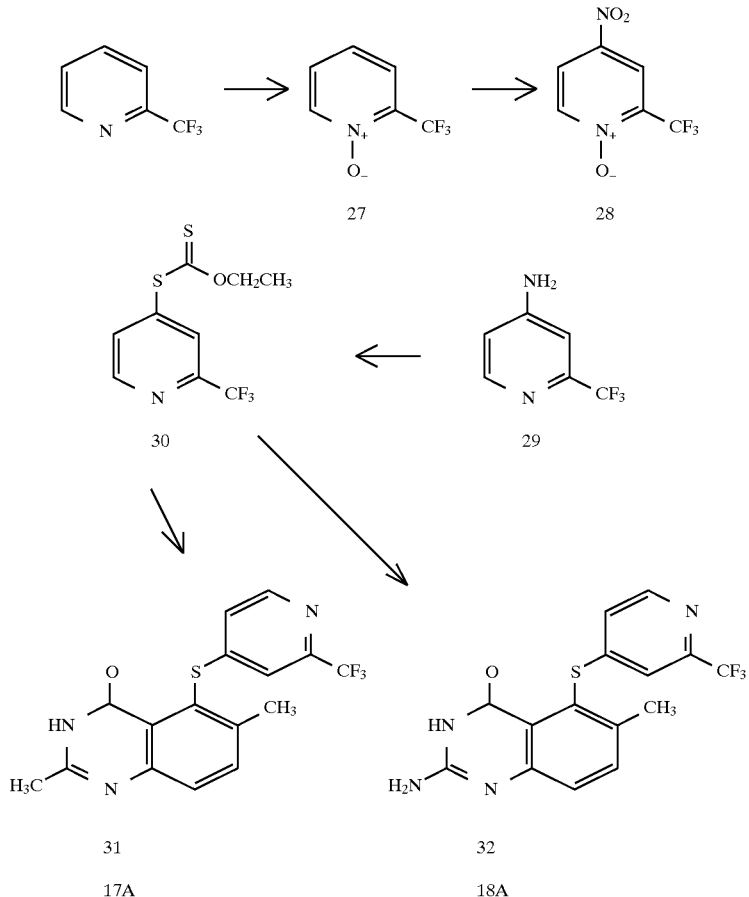

Preparation of Intermediate Compound (27)—2-Trifluoromethylpyridine-N-oxide

Using the procedure to prepare intermediate (22), 2-trifluoromethylpyridine-N-oxide was synthesized in 72% yield starting from 2-trifluoromethylpyridine. (Yellow oil); IR (neat) 3125, 3085, 1721, 1615, 1439, 1329, 1269, 1115, 1071, 1044, 852, 771, 662 cm$^{-1}$; $^1$H NMR (CDCl$_3$) δ 7.38 (t, 1H, J=7.9 Hz), 7.48 (dt, 1H, J=7.0, 2.1 Hz), 7.71 (dd, 1H, J=7.9, 2.1 Hz), 8.35 (d, 1H, J=6.5 Hz). Anal. Calcd. for C$_6$H$_4$F$_3$NO.0.5 H$_2$O: C, 41.87; H, 2.93; F, 33.12; N, 8.14. Found: C, 41.84; H, 2.81; F, 33.19; N, 8.26.

Preparation of Intermediate Compound (28)—4-Nitro-6-trifluoromethylpyridine-N-oxide The nitration of pyridine-N-oxide (27) was carried out using the same method to prepare compound (23), with the following changes. The reaction mixture was heated at 125°–130° C. for 3½ hrs. During work-up, no continuous extraction of the aqueous layer was necessary. The crude solid was purified employing flash column chromatography on silica using ethyl acetate/hexane; 20:80. The product was isolated as a yellow solid (M.P. 112°–114° C.) in 38% yield. IR (KBr) 3416, 3125, 1620, 1591, 1537, 1449, 1354, 1306, 1281, 1165, 1130, 916, 693 cm$^{-1}$; $^1$H NMR (CDCl$_3$) δ 8.28 (dd, 1H, J=7.2, 3.1 Hz), 8.36 (d, 1H, J=7.2 Hz), 8.52 (d, 1H, J=3.1 Hz). Anal. Calcd. for C$_6$H$_3$F$_3$N$_2$O$_3$: C, 34.63; H, 1.45; F, 27.39; N, 13.46. Found: C, 34.86; H, 1.35; F, 27.16; N, 13.66.

Preparation of Intermediate Compound (29)—4-Amino-6-trifluoromethylpyridine

In a Parr hydrogenation bottle, 8.32 g of nitropyridine-N-oxide (28) (0.04 mol) was dissolved in 275 ml of 95% ethanol. The bottle was flushed with argon, and 0.83 g of 10% palladium on activated carbon was added. The bottle was shaken under 35 psi of hydrogen for 45 min on a Parr hydrogenator. At this time, the catalyst was filtered off through a celite pad. The ethanolic filtrate was concentrated under vacuo, and the oil was dissolved in 50 ml of dichloromethane. This solution was filtered through a small pad of silica gel to remove traces of catalyst and carbon. The filtrate was concentrated, and traces of solvent were removed under vacuo. The oil slowly crystallized to give 5.77 g (89% yield) of an analytically pure light orange solid, M.P. 56°–58° C.; IR (KBr) 3501, 3335, 3175, 1657, 1611, 1472, 1373, 1300, 1169, 1117, 993, 850 cm$^{-1}$; $^1$H NMR δ 4.40 (bs, 2H), 6.64 (dd, 1H, J=5.6, 2.3 Hz), 6.89 (d, 1H, J=2.3 Hz), 8.30 (d, 1H, J=5.6 Hz). Anal. Calcd. for C$_6$H$_5$F$_3$N$_2$: C, 44.45; H, 3.11; F, 35.16; N, 17.28. Found: C, 44.56; H, 2.95; F, 35.14; N, 17.28. HRMS calcd. for C$_6$H$_5$F$_3$N$_2$: 162.0405. Found: 162.0402.

Preparation of Intermediate Compound (30)—Ethyl-4-(6-trifluoromethylpyridyl)xanthate A solution of 4.86 g of Amine (29) (0.03 mol) in 30 ml of concentrated H$_2$SO$_4$ was cooled to 0° C. An aqueous solution (30 ml H$_2$O) of 2.69 g NaNO$_2$ (39.0 mmol) was cooled to 0° C. and added dropwise over a period of 15 min. Stirring of the brown mixture was continued at 0° C. for 5 additional minutes. At this time, an ice cold solution of 8.17 g of potassium ethyl xanthate (51.0 mmol) in 30 ml of H$_2$O was added dropwise, maintaining the reaction temperature, between 0°–5° C. The mixture was warmed to room temperature, and dichloromethane (125 ml) was added. The aqueous layer was neutralized to pH7 with solid $Na_2CO_3$. The organic layer was separated, and the aqueous layer was extracted with ethyl acetate (3×50 ml). The organic layers were combined, dried over anhydrous $Na_2SO_4$, and concentrated. The residue was subjected to flash column chromatography using silica gel and a gradient solvent system of ethyl acetate/hexane (2:98, 2.5:97.5, 3:97). Compound (30) was isolated as a yellow oil in 36% yield and was used without further purification. IR (neat) 3061, 2988, 2901, 1738, 1584, 1555, 1406, 1323, 1252, 1184, 1146, 1038, 845, 720 $cm^{-1}$; $^1H$ NMR ($CDCl_3$) δ 1.38 (t, 3H, J=7.1 Hz), 4.66 (q, 2H, J=7.1 Hz), 7.60 (dd, 1H, J=5.0, 1.3 Hz), 7.83 (d, 1H, J=1.0 Hz), 8.77 (d, 1H, J=5.0 Hz). HRMS calcd. for $C_9H_8F_3NOS_2$ (M+1): 268.0077. Found (M+1): 268.0065.

Preparation of Compound 31 (Compound 17A)—3,4-Dihydro-2,6-dimethyl-4-oxo-5-[4-(6-trifluorometlylpyridylthio)]-quinazoline To a solution of 0.67 gm of xanthate (30) (2.5 mmol) in 3 ml MeOH was added 2.5 ml 1N KOH in methanol, and the mixture was stirred for 1½ hr. The mixture was evaporated to dryness, and to the residue was added 10 ml of anhydrous N,N-Dimethylacetamide, 0.25 g quinazoline (6) (10.0 mmol), 0.1 g copper (I) bromide, and 0.1 g copper (I) oxide. The mixture was heated at 90° C. for 6 hrs. and then the solvent was evaporated. The solid was treated with 50 ml of $H_2S$/MeOH solution (20 g/l) for 1 hr. The mixture was filtered, and the filtrate was evaporated to dryness. The solid was purified via flash chromatography on silica using $MeOH/CH_2Cl_2$(5:95) to yield 65 mg (18.5% theory) of a yellow solid: M.P. 240°–245° C.; IR (KBr) 3440, 3190, 3057, 2950, 1675, 1630, 1595, 1321, 1140, 720 $cm^{-1}$; $^1H$ NMR (DMSO-d6) δ 2.28 (s, 3H), 2.42 (s, 3H), 6.97 (d, 1H, J=5.2 Hz), 7.46 (d, 1H, J=1.1 Hz), 7.67 (d, 1H, J=8.4 Hz), 7.84 (d, 1H, J=8.4 Hz), 8.37 (d, 1H, J=5.2 Hz), 12.05 (bs, 1H). HRMS. Calcd. for $C_{16}H_{12}F_3N_3OS$: 351.0656. Found: 351.0653.

Preparation of Compound 32 (Compound 18A)—2-Amino-3,4-dihydro-6-methyl-4-oxo-5-[4-(6-trifluoromethylpyridylthio)]-quinazoline This compound was prepared in 22% yield as described above. Tan solid; M.P. 247°–249° C.; IR (KBr) 3421, 2056, 1650, 1625, 1485, 1419, 1328, 1146, 815, 724 $cm^{-1}$; $^1H$ NMR (DMSO-$d_6$) δ 2.30 (s, 3H), 6.50 (bs, 2H), 6.97 (dd, 1H, J=4.1, 1.2 Hz), 7.30 (d, 1H, J=8.4 Hz), 7.39 (d, 1H, J=1.0 Hz), 7.62 (d, 1H, J=8.6 Hz), 8.36 (d, 1H, J=5.2 Hz), 12.10 (bs, 1H). HRMS calcd. for $C_{15}H_{11}F_3t_4OS$ (M+1): 353.0677. Found (M+1): 353.0684.

Example 6

Preparation of Compound 26A

Compound 26A was prepared according to the following reaction scheme:

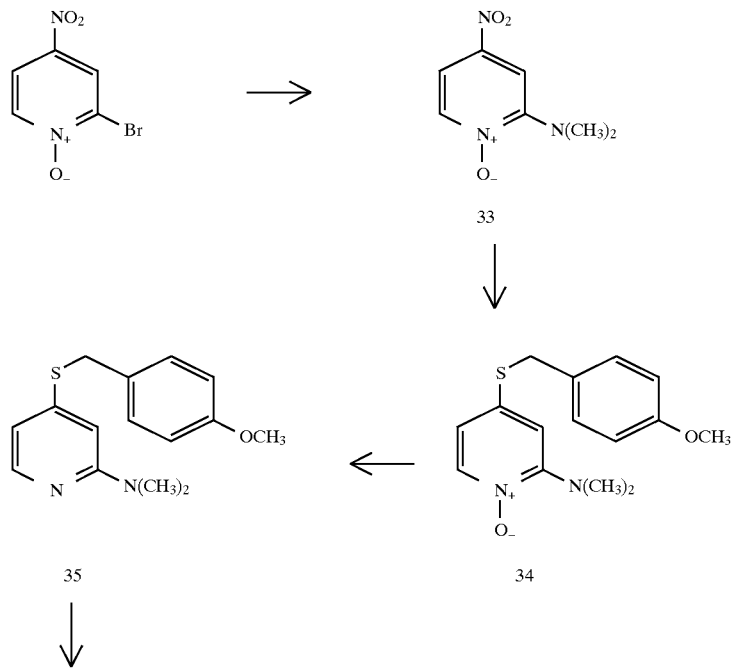

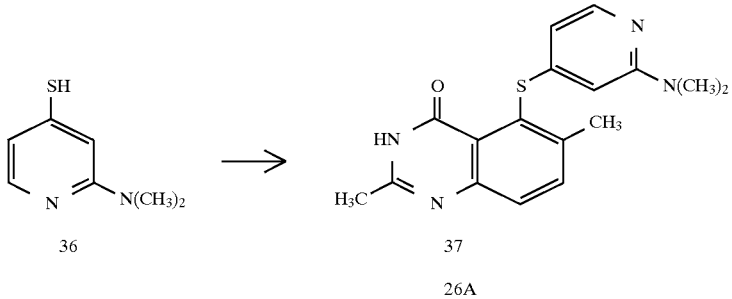

26A

Preparation of Intermediate Compound (33)—6-Dimethylamizno-4-nitropyridine-N-oxide To a solution of 5.0 g (23 mmol) of 2-Bromo-4-nitropyridine-N-oxide[4] dissolved in 75 ml of tetrahydrofuran, was added 1.1 g (24 mmol) dimethylamine. The mixture was stirred for 3 hrs, followed by filtration to remove the dimethylamine-hydrobromide salt. The filtrate was evaporated to dryness, and the crude solid was purified by flash column chromatography on silica using methanol/dichloromethane; 4:96. The product was isolated as an orange solid (M.P. 128°–130° C.) in 83% yield. 1NMR (CDCl$_3$) δ 3.14 (s, 6H), 7.67 (m, 2H), 8.24 (d, 1H, J=7.1 Hz). Anal. Calcd. for C$_7$H$_9$N$_3$O$_3$: C, 45.60; H, 4.95; N, 22.94. Found: C, 46.00; H, 5.00; N, 22.96.

Preparation of Intermediate Compound (34)—6-Dimethylamino-4-(4-methoxybenzylthio)-pyridine-N-oxide To a solution of 1.1 g (7.1 mmol) of 4-Methoxy-α-toluenethiol dissolved in 75 ml anhydrous DMF, was added 0.28 g (7.0 mmol; 60 wt. % dispersion in mineral oil). After stirring for 1 hr, a solution of 1.2 g (6.55 mmol) of pyridine-N-oxide 33 in 25 ml anhydrous DMF was added dropwise. The reaction mixture was stirred for 2 hrs and was then poured into 200 ml H$_2$O. The aqueous solution was extracted with 500 ml diethyl ether, separated, and dried over anhydrous MgSO$_4$. The ether was evaporated to give compound 34 as a tan solid in 63% yield. $^1$H NMR (CDCl$_3$ δ 3.06 (s, 6H), 3.83 (s, 3H), 4.16 (s, 2H), 6.60 (d, 1H, J=2.5 Hz), 6.70 (d, 1H, J=7.0 Hz), 6.90 (d, 2H, J=8.7 Hz), 7.30 (d, 2H, J=8.7 Hz), 8.0 (d, 1H, J=7.0 Hz).

Preparation of Intermediate Compound (35)—6-Dimethylamino-4-(4-methoxybenzylthio)-pyridine The starting pyridine-N-oxide 34, (0.60 g; 2.07 mmol) was reduced using the method to prepare compound 25. Upon completion of the reaction, the mixture was poured into 200 ml H$_2$O, and the pH was adjusted to 7. The aqueous solution was extracted with ethyl acetate (500 ml), and the organic phase was dried over anhydrous Na$_2$SO$_4$, filtered and concentrated. No chromatography was necessary, and the product, 35, was isolated as a yellow solid in 88% yield. $^1$H NMR (CDCl$_3$) δ 3.08 (s, 3H, 3.82 (s, 3H), 4.17 (s, 2H), 6.34 (d, 2H, J=1.3 Hz), 6.48 (d, 1H, J=5.5 Hz), 6.87 (d, 2H, J=8.7 Hz), 7.33 (d, 2H, J=8.7 Hz), 8.0 (d, 1H, J=5.5 Hz).

Preparation of Intermediate Compound (36)—6-Dimethylamino-4-mercaptopyridine

A formic acid (10 ml) solution of pyridine 35 (0.40 g; 1.46 mmol) was cooled to 0° C. To this solution was added 1.2 g of Hg(OAc)$_2$ dissolved in 3 ml H$_2$O. The ice bath was removed, and the reaction mixture was allowed to stir for 12 hours. At this time, the pH was adjusted by the addition of aqueous ammonia. A grey precipitate formed which was filtered, washed with an excess of H$_2$O and air dried. The solid was then taken up in a saturated H$_2$S/methanol solution. A black solid (HgS) formed and was filtered off. The filtrate was evaporated to dryness to yield a yellow solid (89%) which was used without further purification. $^1$H NMR (CDCl$_3$) δ 3.12 (s, 3H), 3.5 (bs, 1H), 6.5 (d, 1H, J=5.3 Hz), 6.57 (d, 1H, J=3.6 Hz), 7.69 (d, 1H, J=5.5 Hz).

Preparation of Compound 37 (Compound 26A)—3,4-Dihydro-2,6-dimethyl-4-oxo-5-[4-(6-dimethylaminopyridylthio)]-quinazoline This compound was prepared from intermediates 6 and 36 using the exact procedure to generate compound 9 (8A). The crude product was purified by flash column chromatography on silica gel using MeOH/CH$_2$Cl$_2$ (8:92) to give a tan solid in 21% yield. $^1$NMR (DMSO-d$_6$) δ 1.97 (s, 3H), 2.08 (s, 3H), 2.56 (s, 3H), 5.55 (d, 1H, J=5.4 Hz), 5.82 (d, 1H, J=1.2 Hz), 7.27 (d, 1H, J=8.4 Hz), 7.44 (d, 1H, J=5.2 Hz), 7.45 (d, 2H, J=8.4 Hz), 12.75 (bs, 1H). Anal. Calcd. for C$_{17}$H$_{18}$N$_4$OS.0.5H$_2$O: C, 60.82; H, 5.6; N, 16.69; S, 9.54. Found: C, 61.01; H, 5.63; N, 16.55; S, 9.42.

Example 7

Preparation of Compounds 27A and 28A

Compounds 27A and 28A were prepared according to the following reaction scheme:

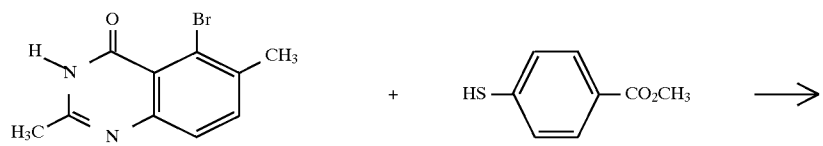

6

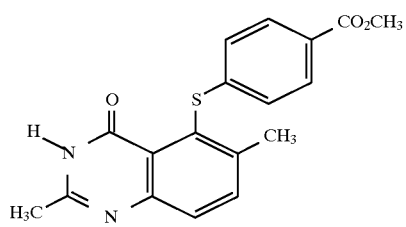 38

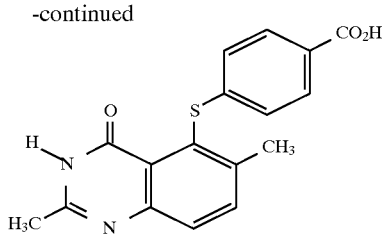 39

28A

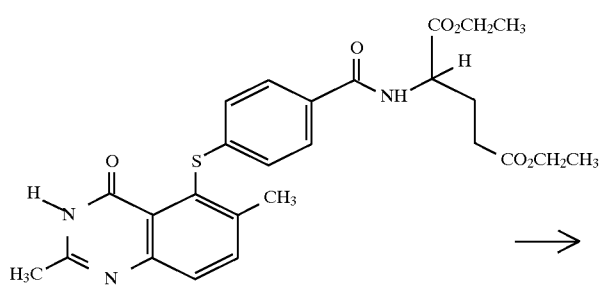 40

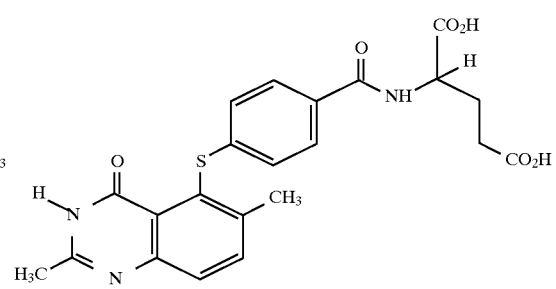 41

27A

Preparation of Intermediate Compound (38)—
Methyl-4-[3,4-dihydro-2,6-dimethyl-4-oxo-5-quinazolinyl)thio]-benzoate This compound was prepared from intermediate 6 and methyl-4-mercaptobenzoate [P. R. Marsham et al., *J. Med. Chem.* 34 2209 (1991); and E. Campaigne, et al., *J. Org. Chem.* 27 2835 (1962)] using the procedure to synthesize compound 9 (8A). After heating the mixture at 90° C. for 16 hrs. the DMA was removed under vacuum, and the solid residue was suspended in methanol. To this stirred suspension, a stream of gaseous $H_2S$ was bubbled slowly in for approximately 5 min. A dark solid (CuS) formed which was removed by filtration. The methanolic filtrate was concentrated, and the product was purified by flash column chromatography on silica with methanol/dichloromethane; 5:95; to give a tan solid in 85% yield. $^1H$ NMR (DMSO-$d_6$) δ 2.26 (s, 3H), 2.43 (s, 3H), 3.75 (s, 3H), 6.94 (d, 2H, J=8.4 Hz), 7.22 (d, 1H, J=8.5 Hz), 7.52 (d, 1H, J=8.5 Hz), 7.71 (d, 2H, J=8.4 Hz), 11.7 (bs, 1H). HRMS calcd. for $C_{18}H_6N_2O_3S$: 340.0898. Found: 340.0882.

Preparation of Compound (39) (Compound 28A)—
4-[(3,4-Dihydro-2,6-dimethyl-4-oxo-5-quinazolinyl)thio]-benzoic acid An ethanolic solution (5 ml) consisting of 0.186 g (0.55 mmol) of methyl ester 38 and 0.5 ml of aqueous 1N NaOH was heated at 50° C. for 4 hrs. At this time, the solution was evaporated to dryness, and the sodium salt was dissolved in 3 ml $H_2O$. This solution was carefully acidified to pH 4 with concentrated HCl. The free acid which precipitated was filtered and washed with 5 ml of cold $H_2O$. The solid was dried in a desicator over $CaSO_4$ to yield 0.15 g (84%) of acid 39 (28A) as a beige solid. $^1H$ NMR (DMSO-$d_6$) δ 2.29 (s, 3H), 2.45 (s, 3H), 7.0 (d, 2H, J=8.5 Hz), 7.44 (d, 1H, J=8.6 Hz), 7.71 (d, 2H, J=8.4 Hz), 7.74 (d, 1H, J=8.3 Hz). HRMS calcd. for $C_{17}H_{14}N_2O_3S$: 326.0742. Found: 326.0725.

Preparation of Intermediate Compound (40)—
Diethyl-N-[4-((3 4-dihydro-2,6-dimethyl-4-oxo-5-quinazolinyl)thio)benzoyl]-L-glutamate Benzoic acid 39 (60.0 mg; 18.4 mmol) and (L)-glutamic acid diethyl ester.HCl (0.144 g; 0.6 mmol) were dissolved in 5 ml of anhydrous DMF and cooled to 0° C. To the stirred solution was added diphenylphosphoryl azide (0.15 ml; 0.7 mmol). After 15 min, 0.2 ml (1.4 mmol) of triethylamine was added, and the reaction mixture was allowed to stir for 12 hrs at room temperature. The solvent was then removed under vacuum, and the remaining solid wets taken up in 5 ml $H_2O$. The pH was carefully adjusted to 6 with concentrated HCl, and the aqueous solution was extracted with $CHCl_3$ (3×10 ml). The organic layers were combined, dried over $MgSO_4$, filtered and evaporated to dryness. The product was purified by flash chromatography on silica using methanol/dichloromethane; 10:90. A tan solid (78.0 mg; 82%) was isolated. $^1H$ NMR (DMSO-$d_6$) δ 1.11 (m, 6H), 1.61 (m, 2H), 1.79 (m, 2H), 2.26 (s, 3H), 2.37 (s, 3H), 3.26 (m, 1H), 4.05 (m, 4H), 6.96 (d, 2H, J=8.4 Hz), 7.55 (d, 1H, J=8.5 Hz), 7.64 (d, 2H, J=8.4Hz), 7.71 (d, 1H, J=8.5 Hz), 8.60 (d, 1H, J=5.3 Hz), 12.10 (bs, 1H). HRMS calc for $C_{26}H_{29}N_3O_6S$ (M+1): 512.1843. Found (M+1): 512.1855.

Preparation of Compound (41) (Compound 27A)—
N-[4-((3,4-Dihydro-2,6-dimethyl-4-oxo-5-quinazolinyl)thio)benzoyl]-L-glutamic acid Diethyl ester 40 (78.0 mg; 0.15 mmol) was dissolved in 5 ml of ethanol, and to this solution was added 0.5 ml of an aqueous 1N NaOH solution. The reaction mixture was stirred at 50° C. for 3 hrs, where upon disappearance of starting by TLC the solution was evaporated to dryness. The disodium salt was further dissolved in 2 ml of $H_2O$ and acidified to pH 4 with concentrated HCl. The solid was filtered upon precipitation and washed with 5 ml of cold $H_2O$. The final product was dried under vacuum over $CaSO_4$ yielding 50 mg (72%) of an off white solid. $^1H$ NMR (DMSO-$d_6$) δ 1.95 (m, 2H), 2.05 (m, 2H), 2.26 (s, 3H), 2.46 (s, 3H), 4.40 (m, 1H), 6.93 (d, 2H, J=8.4 Hz), 7.55 (d, 1H, J=8.4 Hz), 7.65 (d, 2H, J=8.5 Hz), 7.71 (d, 1H, J=8.4 Hz), 8.40 (bd, 1H, J=5.4 Hz), 12.00 (bs, 1H). Anal. Calcd. for $C_{22}H_{21}N_3C_6S \cdot 2HCl$: C, 50.05; H, 4.36; N, 7.96; S, 6.06. Found: C, 50.38; H, 4.69; N, 7.60; S, 5.77.

Example 8

Preparation of Compounds 3A and 5A

Compounds 3A and 5A were prepared according to the following reaction scheme:

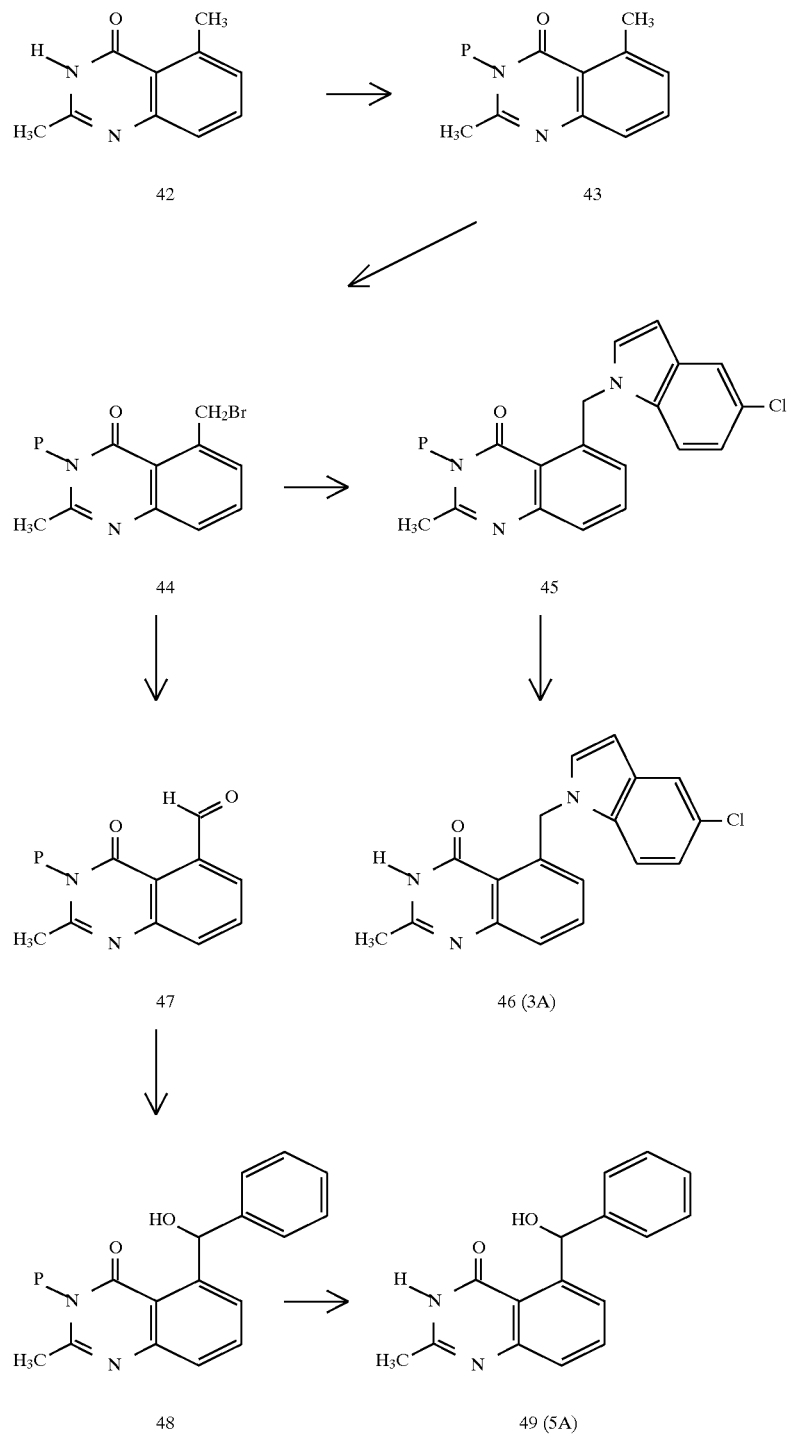

Preparation of Intermediate Compound (42)—3,4-Dihydro-2,5-dimethyl-4-oxo-quinazolinone.

This compound was prepared via its corresponding benzoxazinone from 6-methylanthranilic acid using the procedure to prepare quinazolinone (6). The solid was recrystallized from ethanol. (M.P. 258°–259° C.). $^1$H NMR (CDCl$_3$) δ 2.53 (s, 3H), 2.89 (s, 3H), 7.20 (d, 1H, J=7.3 Hz), 7.50 (d, 1H, J=8.0 Hz), 7.59 (dd, 1H, J=8.1, 7.3 Hz), 11.52 (bs, 1H). Anal. Calcd. for C$_{10}$H$_{10}$N$_2$: C, 68.95; H, 5.79; N, 16.08. Found: C, 69.03; H, 5.82; N, 16.03.

Preparation of Intermediate Compound (43)—2,5-Dimethyl-3-[2'-(trimethylsilyl) ethoxymethyl]-quinazolin-4-one.

To 70 ml of dry DMF was added 2.175 g (12.5 mmol) of quinazolinone (42). The mixture was cooled to 0° C., and 0.55 g of NaH (13.75 mmol; 60% oil dispersion) was added portionwise with stirring. The green colored mixture was allowed to warm to room temperature, and stirring was continued until gas (H$_2$) evolution ceased. At this time, the solution was recooled to 0° C., and 2-(Trimethylsilyl) ethoxymethylchloride(SEM-Cl) (2.45 ml; 13.75 mmol) was added dropwise. A cloudy precipitate (NaCl) began to form.

After all the SEM-Cl was added, the ice bath was removed, and the reaction mixture was stirred at room temperature for 12 hrs. The mixture was poured into H$_2$O (300 ml) and extracted with hexanes (3×150 ml). The organic layers were combined and dried over anhydrous MgSO$_4$. Upon filtration and concentration, a white powder began to form. The solid was removed by filtration and was shown to be the starting material, (42), by TLC and $^1$H NMR. The filtrate was concentrated to give a pale yellow oil which was passed through a flash silica gel column using diethyl ether/petroleum ether; 1:1, yielding 3.0 g (79%) of product (43) as an oil. IR (neat) 2980, 1675, 1600, 1572, 1460, 1380, 1287, 1248, 1075, 858, 835 cm$^{-1}$; $^1$H NMR (CDCl$_3$) δ 0.00 (5, 9H), 0.95 (dd, 2H, J=8.2, 7.2 Hz), 2.66 (s, 3H), 2.84 (s, 3H), 3.68 (dd, 2H, J=8.2, 7.1 Hz), 5.52 (s, 2H), 7.18 (d, 1H, J=6.8 Hz), 7.43 (dd, 1H, J=8.0, 0.3 Hz), 7.55 (dd, 1H, J=8.0, 7.5 Hz).

Preparation of Intermediate Compound (44)—5-Bromomethyl-2-methyl-3-[2'-(trimethylsilyl) ethoxymethyl]-quinazolin-4-one.

The SEM protected quinazolinone (43) (2.28 g, 7.5 mmol) was dissolved in 30 ml CCl$_4$. To the solution was added 1.417 g (8.23 mmol) of N-bromosuccinimide. The pale yellow solution was heated to a gentle reflux until almost completely homogeneous. At this time, the benzylic bromination reaction was initiated with a 200 watt lamp. The reaction began to reflux more vigorously and turned a deep orange color. After approximately 15 min, the color faded and succinimide precipitated. The reaction was cooled, filtered and washed with 25 ml CCl$_4$. The filtrate was washed with minimal H$_2$O (~5 ml), separated, dried over MgSO$_4$, refiltered and concentrated leaving a solid residue which was further purified by flash column chromatography on silica using a gradient system of diethyl ether/petroleum ether; 15/85; 20/80; 25/75; 30/70; 35/65. The pure bromide (1.25 g) was isolated as a white sold in 43% yield (54% based on recovered (43): M.P. 78°–80° C. IR (KBr) 3085, 2980, 1675, 1608, 1382, 1340, 1293, 1248, 1075, 860, 630, 710 cm$^{-1}$; $^1$H NMR (CDCl$_3$) δ 0.00 (s, 9H), 0.93 (dd, 2H, J=8.3, 7.1 Hz), 2.66 (s, 3H), 3.68 (dd, 2H, J=8.4, 7.1 Hz), 5.24 (s, 2H), 5.55 (s, 2H), 7.38 (dd, 1H, J=7.2, 1.5 Hz), 7.55 (dd, 1H, J=7.5, 1.5 Hz), 7.61 (dd, 1H, J=7.5, 7.2 Hz). Anal. Calcd. for C$_{16}$H$_{23}$BrN$_2$O$_2$Si: C, 50.12; H, 6.04; Br, 20.84; N, 7.30. Found: C, 50.35; H, 6.06; Br, 21.01; N, 7.32.

Preparation of Intermediate Compound (45)—5-Chloro-N-[2'-methyl-3'-(2"-(trimethylsilyl) ethoxymethyl)-4'-oxo-5'-quinazolyl)methyl]indole.

In 6.5 ml anhydrous DMF, 0.417 g (2.75 mmol) of 5-chloroindole was dissolved. The stirred solution was cooled to 0° C., and 0.11 g (2.75 rTmol, 60% oil dispersion) of NaH was added portionwise. Once the anion was formed (~30 min.), 0.958 g (2.5 mmol) of Bromomethylquinazoline (44), dissolved in 0.5 ml anhydrous DMF was syringed in. The reaction was complete upon disappearance of starting materials by TLC (40% ether/petroleum ether). Ice was added to quench excess anion, followed by 20 ml H$_2$O. This was then extracted with diethyl ether (3×50 ml), and the organic layers were combined and dried over anhydrous MgSO$_4$. Filtration and evaporation gave a residue which was purified by flash column chromatography on silica using diethyl ether/petroleum ether: 40:60. A white crystalline solid was isolated (0.927 g; 82%; M.P. 98°–99° C.). IR (KBr) 3095, 2980, 1715, 1595, 1565, 1440, 1345, 1280, 1245, 1175, 1060, 932, 834, 795, 755, 720, 612 cm$^{-1}$; $^1$H NMR (CDCl$_3$) δ 0.03 (s, 9H), 1.00 (m, 2H), 2.71 (s, 3H), 3.74 (m, 2H), 5.55 (s, 2H), 6.04 (s, 2H), 6.25 (dd, 1H, J=7.4, 1.3 Hz), 6.54 (dd, 1H, J=3.1, 0.3 Hz), 7.08 (m, 2H), 7.18 (d, 1H, J=3.1 Hz), 7.45 (m, 2H), 7.63 (dd, 1H, J=1.6, 1.0 Hz). Anal. Calcd. for C$_{24}$H$_{28}$ClN$_3$O$_2$Si: C, 63.48; H, 6.21; Cl, 7.80; N, 9 25. Found: C, 63.41; H, 6.13; Cl, 7.91; N, 9.19.

Preparation of Compound (46) (Compound 3A)—5-Chloro-N-[(3,4-dihydro-2-methyl-4-oxo-5-quinazolyl)methyl]indole.

The SEM protected quinazoline (45) (0.75 g; 1.65 mmol) was dissolved in 1.5 ml THF. To this solution was added 6a0 ml of a 1.0M THF solution of tetrabutylammonium fluoride. With stirring, the mixture was heated to 50° C. for 7 hrs. The solution was cooled to room temperature, and 20 ml of H$_2$O was added. This was then extracted with a large excess (200 ml) of ethyl acetate. The organic layer was separated and dried over anhydrous MgSO$_4$, filtered and concentrated leaving a solid residue which was recrystallized from ethyl acetate yielding product (46) (Compound 3A) in 46%. M.P. 251°–2529° C.; $^1$H NMR (DMSO-d$_6$) δ 2.34 (s, 3H), 6.08 (s, 2H), 6.14 (dd, 1H, J=7.3, 1.0 Hz), 6.53 (dd, 1H, J=3.0, 0.5 Hz), 7.05 (dd, 1H, J=8.7, 2.1 Hz), 7.34 (d, 1H, J=8.8 Hz), 7.46 (m, 2H), 7.56 (d, 1H, J=3.1 Hz), 7.64 (d, 1H, J=2.1 Hz), 12.30 (bs, 1H). Anal. Calcd. for C$_{18}$H$_{14}$ClN$_3$O.0.1 EtOAc: C, 66.45; H, 4.49; Cl, 10.66; N, 12.63. Found: C, 66.68; H, 4.62; Cl, 10.95; N, 12.27. HRMS Calcd. for C$_{18}$H$_{14}$ClN$_3$O: 323.0825. Found: 323.0813.

Preparation of Intermediate Compound (47)—5-Formyl-2-methyl-3-[2'-(trimethylsilyl)ethoxymethyl]-quindzolin-4-one.

To a solution of NaOEt in ethanol, prepared by dissolving 34.5 mg (1.5 mmol) of sodium metal in 1.5 ml of absolute ethanol, was added 0.14 ml (1.56 mmol) of 2-nitropropane. 0.575 g (1.5 mmol) of Bromomethylquinazoline (44) was added, and the reaction was stirred and heated at 40° C. for 12 hrs. At this time, 10 ml of H$_2$O was added, and the mixture was extracted with diethyl ether (2×50 ml). The organic layers were separated, dried over anhydrous Na$_2$SO$_4$, filtered and concentrated. The residue was purified by flash column chromatography with 70% ether/pet. ether yielding 0.346 g (73%) of aldehyde (47) as a white solid. $^1$H HMR (CDCl₃) δ 0.00 (s, 9H), 0.96 (m, 2H), 2.73 (s, 3H), 3.75 (m, 2H), 5.58 (s, 2H), 7.82 (m, 2H), 7.87 (m, 1H), 11.17 (s, 1H).

Preparation of Intermediate Compound (48)—5-(a-Hydroxytolyl)-2-methyl-3-[2'-(trimethylsily) ethoxymethyl]-quinazolin-4-one.

Aldehyde (47) (0.72 g; 2.26 mmol) was dissolved in 9.0 ml of anhydrous THF under an argon atmosphere. The stirred solution was cooled to −78° C., and phenylmagnesium bromide (0.83 ml; 3.0M in diethyl ether) was introduced dropwise. The reaction mixture was allowed to warm to room temperature, and stirring was continued for 1 hr. To quench the reaction, 10 ml of sat. ag. NH₄Cl was added. The mixture was then extracted with diethyl ether (3×50 ml), separated, combined, dried over anhydrous MgSO4, filtered and concentrated. Purification of the residue by flash column chromatography on silica with ether/pet. ether; 60:40; supplied 0.621 g of the benzylic alcohol (48), as a colorless oil in 74% yield. IR (neat) 3380, 3070, 3035, 2960, 2900, 1660, 1600, 1540, 1445, 1245, 1135, 1075, 915, 830, 695 cm⁻¹; ¹H NMR (CDCl₃) δ 0.00 (s, 9H), 0.88 (m, 2H), 2.68 (s, 3H), 3.54 (m, 2H), 5.50 (s, 2H), 5.77 (d, 1H, J=8.3 Hz), 6.36 (d, 1H, J 8.0 Hz), 7.25 (m, 4H), 7.30 (m, 2H), 7.60 (dd, 1H J=8.2, 1.5 Hz), 7.67 (dd, 1H, J=7.7, 7.2 Hz). Anal. Calcd. for C₂₂H₂₈N₂O₃Si: C, 66.63; H, 7.11; N, 7.06. Found: C, 66.66; H, 6.97; N, 7.00.

Preparation of Compound (49) (Compound 5A)—3,4-Dihydro-2-methyl-4-oxo-5-(α-hydroxytolyl)-quinazoline.

Following the same procedure to prepare compound (46) (Compound 3A), the SEM-quinazoline (48) was deprotected using 3.0 eq. of tetrabutylammonium fluoride at 50° C. for 4 hrs. Quinazoline (49) (Compound 5A) was isolated as a white solid in 38% yield after purification by flash chromatography on silica using methanol/dichlormethane; 5:95· ¹H NMR (DMSO-d₆) δ 2.29 (s, 3H), 5.93 (d, 1H, J=5.1 Hz), 7.15 (m, 1H), 7.21 (m, 3H), 7.27 (m, 2H), 7.45 (dd, 1H, J=5.6, 3.9 Hz), 7.73 (m, 2H), 12.06 (bs, 1H).

Example 9

Preparation of Compounds 4A and 6A

Compounds 4A and 6A were prepared according to the following reaction scheme:

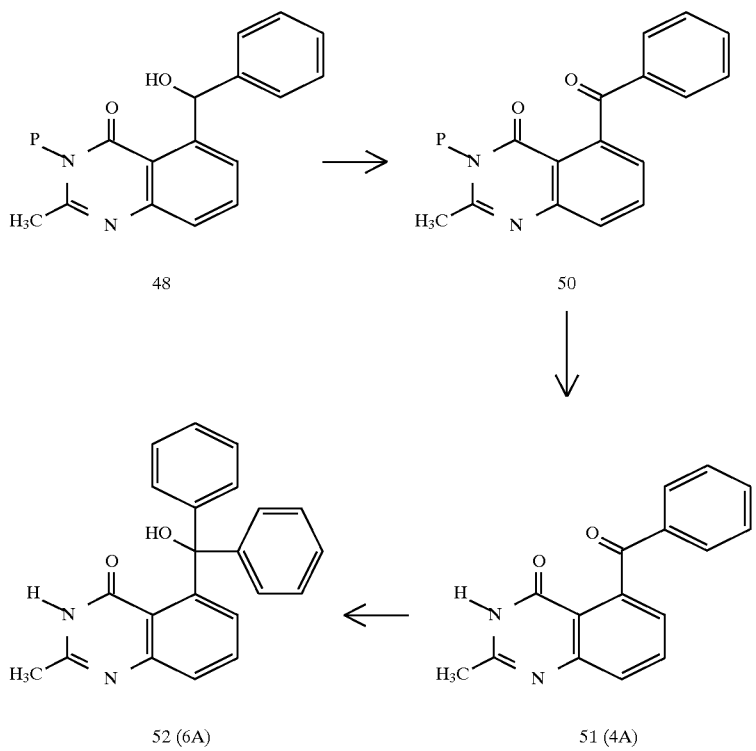

Preparation of Intermediate Compound (50)—5-Benzoyl-2-methyl-3-[2'-(trimethylsilyl) ethoxymethyl]quinazolin-4-one.

Benzylic alcohol (48) (0.569 g; 1.43 mmol) was taken up in 1.8 ml of dry CH₂Cl₂ and stirred under an inert atmosphere. Activated Mno₂ (1.43 g) was added, and the progress of the reaction was followed by TLC (ether/pet. ether; 70/30). Upon disappearance of starting material, the black mixture was filtered through a pad of celite, and the pad was washed thoroughly with CH₂Cl₂ (100 ml). The filtrate was dried over anhydrous Na₄SO₄ filtered and concentrated, leaving 0.48 g (85%) as a white solid that was analytically pure. M.P. 124°–125° C.; IR (KBr) 3010, 2955, 2900, 1660, 1560, 1440, 1345, 1292, 1245, 1178, 1060, 920, 825, 685 cm⁻¹; ¹H NMR (CDCl₃) δ −0.10 (s, 9H), 0.82 (m, 2H), 2.70 (s, 3H), 3.48 (m, 2H), 5.42 (s, 2H), 7.31 (dd, 1H, J=7.1, 1.3 Hz), 7.39 (m, 2H), 7.51 (m, 1H), 7.72 (m, 1H), 7.74 (m, 2H), 7.80 (dd, 1H, J=8.2, 7.1 Hz). Anal. Calcd. for C₂₂H₂₆N₂O₃Si: C, 66.97; H, 6.64; N, 7.10. Found: C, 66.76; H, 6.52; N, 6.95.

Preparation of Compound (51) (Compound 4A)—
5-Benzoyl-3,4-dihydro-2-methyl-4-oxo-quinazoline.

The protected quinazoline (50) (0.255 g; 0.64 mmol) was added to 7.0 ml of 1:1 THF: 2N HCl. The mixture became homogeneous when heated just under ref lux. After 3 hrs, a white precipitate formed. The mixture was cooled to room temperature, and 10 ml of cold $H_2O$ was added. With vigorous stirring, an excess of sat. aq. $NaHCO_3$ was added. The solid was filtered off and washed thoroughly with cold $H_2O$ (2×10 ml). The solid was dried under vacuum over activated silica gel desiccant. The analytically pure white solid (0.14 g) was isolated in 83% yield. M.P. 288°–289° C.; IR (KBr) 3175, 3030, 2880, 1660, 1635, 1325, 1265, 880, 825, 780, 725 cm$^{-1}$; $^1$H NMR (DMSO-d$_6$) δ 2.35 (s, 3H), 7.30 (dd, 1H, J=7.3, 1.0 Hz), 7.44 (m, 2H), 7.58 (m, 3H), 7.71 (dd, 1H, J=8.3, 1.0 Hz), 7.85 (dd, 1H, J=8.1, 7.3 Hz), 12.22 (bs, 1H). Anal. Calcd. for $C_{16}H_{12}N_2O_2$: C, 72.71; H, 4.57; N, 10.60. Found: C, 72.61; H, 4.70; N, 10.39.

Preparation of Compound (52) (Compound 6A)—3,4-Dihydro-5-(α-diphenyl-hydroxymethyl)-2-methyl-4-oxo-quinazoline.

Under an argon atmosphere, 79.3 mg (0.3 mmol) of ketone (51) (Compound 4A) was suspended in 5.0 ml of anhydrous THF. The stirred suspension was cooled to 0° C., and 0.375 ml of phenyllithium (2.0M in 70:30/cyclohexane:ether) was syringed into the reaction vessel dropwise. Upon addition of the first equivalent of reagent, the starting substrate solubilized. When the addition was completed, the ice bath was removed, and the reaction was allowed to stir for 1 hr. The solution was quenched with ice-$H_2O$ (~2.0 ml) and poured into 50 ml of $CH_2Cl_2$. The aqueous layer was extracted two more times with $CH_2Cl_2$ (50 ml), the organic layers were combined and dried over anhydrous $MgSO_4$. The drying agent was filtered off, and the filtrate was concentrated and purified by flash column chromatography on silica with $CH_3OH:CH_2Cl_2/4:96$. The product was isolated as a white solid (57 mg; 58%). $^1$H NMR (DMSO-d$_6$) δ 2.33 (s, 3H), 6.55 (dd, 1H, J=5.4, 3.6 Hz), 7.07 (m, 4H), 7.23 (m, 6H), 7.59 (m, 2H), 8.73 (s, 1H), 12.46 (bs, 1H). HRMS Calcd. for $C_{22}H_{18}N_2O_2$: 342.1368. Found: 342.1366.

BIOCHEMICAL AND BIOLOGICAL EVOLUTION

Determination of Inhibition Constants Against 5,10-Methylene-tetrahydrofolate for the Enzyme Thymidylate Synthase Thymidylate synthase activity was measured using a modification of the tritium release method of Lomax and Greenberg [M. I. S. Lomax and G. R. Greenberg, *J. Biol. Chem.* 242 109 (1967)]. Inhibition constants, $K_i$, slope and $K_i$, intercept [W. W. Cleland, *Biochim. Biophys.* Acta 67 173 (1963)], were determined against the cofactor (6R, 6S)-5,10-methylene-tetrahydrofolate which was generated in situ by reaction of tetrahydrofolate with formaldehyde [R. G. Kallen and W. P. Jencks, *J. Biol. Chem.* 241 5851 (1966)]. The cofactor was present as the variable substrate under conditions of saturating radiolabelled 2'-deoxyuridine 5'-monophosphate (dUMP). Assays in a total volume of 0.1 mL contained 50mM Tris @ pH 7.6, 10 mM DTT (dithiothreitol), 1 mM EDTA (ethylenediaminetetraacetic acid), 25 mM $MgCl_2$, 15 mM formaldehyde, ±1% DMSO (depending on the solubility of the compound), 25 μM [5-$^3$H] dUMP (specific activity 2×10$^8$ cpm/μmol), tetrahydrofolate (eight concentrations ranging from 5 μM to 300 μM) and enzyme (=30 ng for *E. coli* TS and =60 ng for human TS). Assays of human TS also contained 1–5 μg/mL bovine serum albumin to stabilize the protein. Reactions were initiated by the addition of enzyme and were carried out for 5 minutes at 24° C., and then quenched by the addition of charcoal (15 mg in 0.1 mL $H_2O$). The quenched samples were centrifuged at 10,000 rpm for 12–15 min at 40° C. to remove unreacted dUMP which had bound to the charcoal, and 0 1 mL of the supernatant was counted by liquid scintillation in the presence of 5 mL ecolume to determine the release of tritium label from the 5-position of the dUMP. A standard curve was established in the absence of inhibitor, and three additional curves containing inhibitor at approximately ½ to 2 times the $K_i$ were determined. Experimental results were analyzed by EZ-FIT, a nonlinear regression analysis program (Perrella Scientific, Springfield, Pa.) which was used to fit all data points simultaneously to a mixed noncompetitive inhibition scheme. The results obtained are shown in the Table. The first entry for each compound is the $K_i$, slope and the entry underneath is the $K_i$, intercept.

In Vitro Testing to Determine Inhibition of Growth of Tumor Cells

Cellular growth in the presence of the compounds in question was assessed using three cell lines: the L1210 murine leukemia (ATCC CCL 219), CCFR-CEM, a human lymphoblastic leukemia line of T-cell origin (ATCC CCL 119), and a thymidine kinase-deficient human colon adenocarcinoma, $GC_3$/M TK$^-$ (supplied by Drs. P. J. and J. A. Houghton, St. Jude Childrens Research Hospital, Memphis, Tenn.). Cell lines were maintained in RPMI 1640 medium containing 5% (L1210, CCRF-CEM) or 10% ($GC_3$/M TK$^-$) heat-inactivated fetal bovine serum without antibiotics.

$IC_{50}$ values were determined in 150 μL microcultures each containing 1500 (L1210) or 10,000 (CCRF-CEM, $GC_3$/M TK$^-$) cells established in 96 well plates in growth medium supplemented with 50 U/mL penicillin and 50 μg/mL streptomycin. Growth was measured over 3 days (L1210) or 5 days (CCRF-CEM, $GC_3$/M TK$^-$) of continuous exposure to varying concentrations of each test compound, added 4 h. after initial cell plating, by the MTT-tetrazolium reduction assay of T. J. Mosmann [*J. Immunol. Meth.* 65 55 (1983)] modified according to Alley et al. [*Cancer Res.* 48 589 (1988)]. Water insoluble derivatives were dissolved in DMSO and diluted to a final concentration of 0.5% solvent in cell cultures.

The results obtained from this procedure are-shown below in the Table 2. [Although Table 2 indicates that certain compounds do not demonstrate particularly good TS inhibition, these compounds are of potential interest in that they may demonstrate other antitumor, activity such as toxicity to L1210 cells in tissue culture.]

TABLE 2

| | KiData (μM) | | Cell Culture (IC50μM) | | |
|---|---|---|---|---|---|
| | E. coli | Human | L1210 | CCRF-CEM | GC3-M (TK-) |
| 1A | >100 | >100 | — | — | — |
| 2A | >10 | >10 | — | — | — |
| 3A | >3 | >3 | — | 10% >12.3 | 20% >12.7 |

TABLE 2-continued

| | KiData (μM) | | Cell Culture (IC50 μM) | | |
|---|---|---|---|---|---|
| | E. coli | Human | L1210 | CCRF-CEM | GC3-M (TK-) |
| 4A | — | — | — | — | — |
| 5A | — | — | — | — | — |
| 6A | >10 | >10 | 2.3 | 4.0 | >4.98 |
| 7A | 38 ± 5 | 2.1 ± 0.5 | 14 68% @ 20um | 37% @ >26.9 | none @ >26.9 |
| 8A | 0.89 ± 0.28 | 0.062 ± 0.23 | 3.5 | 5.2 | 6.0 |
| 9A | 0.22 ± 0.07 | 0.13 ± 0.04 | 1.8 | 2.1 | 4.5 |
| 10A | 0.75 ± 0.08 | 0.083 ± 0.011 | 3.0 | 2.9 | >4.0 |
| 11A | 21 ± 13 | 2.0 ± 0.4 | none @ >3.33 | 17% @ >3.33 | none @ >3.33 |
| 12A | 0.55 ± 0.05 | 0.07 ± 0.001 | 4.2 | 4.2 | 5.0 |
| 13A | 3.9 ± 0.9 | 0.64 ± 0.01 | 21 | 26 | 32 |
| 14A | 0.15 ± 0.03 | 0.017 ± 0.008 | 1.0 | 0.81 | 1.0 |
| 15A | 190 ± 130 | 19 ± 11 | 27% @ >50 | 40% @ >50 | 4% @ >50 |
| 16A | 0.76 ± 0.12 | 0.048 ± 0.006 | 3.1 | 3.8 | >5.0 |
| 17A | 0.54 ± 0.07 | 0.13 ± 0.03 | 8.1 | 8.6 | 15.0 |
| 18A | — | — | 1.8 | 33% @ >2.0 | 33% @ >2.0 |
| 19A | — | — | — | — | — |
| 20A | 311 ± 99 | 61 ± 17 | 40% @ >50 | 20% @ >50 | none @ >50 |
| 21A | >80 | 190 ± 25 | 28% @ >50 | 42% @ >50 | none @ >50 |
| 22A | 9.3 ± 1.6 | 1.1 ± 0.3 | 4% @ >2.5 | none @ >2.5 | none @ >2.5 |
| 23A | — | 0.13 ± 0.009 | 3.5 | 5.1 | 6.1 |
| 24A | — | 0.023 ± 0.001 | 0.55 | 1.1 | 1.2 |
| 25A | — | 0.022 ± 0 | 0.59 | 1.1 | 1.7 |
| 26A | — | 0.079 ± 0 | 4.05 | 10.5 | 18.0 |
| 27A | — | 0.00795 ± 0 | 1.05 | 0.99 | 4.1 |
| 28A | — | 0.115 ± 0 | 27% @ >50 | none @ >50 | none @ >50 |
| 29A | 1.1 ± 0.2 | 0.12 ± 0.02 | 8.0 | 10.5 | >12.5 |
| 30A | 0.14 ± 0 | 0.011 ± 0 | 1.6 | 0.88 | 1.5 |
| 31A | 21.0 ± 6 | 51.0 ± 2.2 | 48.0 | >50 | >50 |
| 32A | >10 | >10 | >10 | 6.0 | 30% @ >10 |
| 33A | 36 ± 1.5 | 47 ± 17 | 25.0 | 18.0 | 20% @ >25 |

* — (Assay not performed)

While the invention has been described in detail and with reference to specific embodiments thereof, it will be apparent to one skilled in the art that various changes and modifications can be made therein without departing from the spirit and scope thereof. Thus, it is intended that the present invention cover the modifications and variations, provided they come within the scope of the appended claims and their equivalents.

We claim:

1. A pharmaceutical composition, comprising: an effective amount of a quinazoline compound according to formula I, or a pharmaceutically acceptable salt thereof, to inhibit growth and proliferation of cells of higher organisms and microorganisms, the compound according to formula I represented as follows:

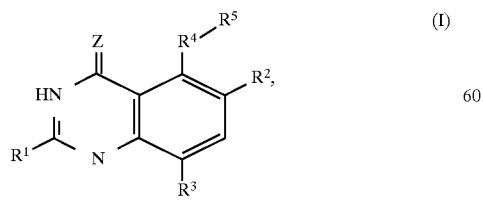

(I)

wherein:

$R^1$ represents hydrogen, halogen, alkyl, —OH, —O-alkyl, —O-(aryl or heteroaryl), —S-alkyl, —S-(aryl or heteroaryl), —NH$_2$, —NH-alkyl, —N-(alkyl)$_2$, —NHCHO, —NHOH, —NHO-alkyl, —NHNH$_2$, substituted —NHNH$_2$, —NHC(=NH)NH$_2$, —NHC(=NH)alkyl, fluoroalkyl, cycloalkyl, alkenyl, alkynyl, aryl, or heterocycle;

$R^2$ and $R^3$, which may be the same or different, represent hydrogen, halogen, alkyl, cycloalkyl, —OH, —O-alkyl, —S-alkyl, —NH$_2$, —NH-alkyl, —N-(alkyl)$_2$, —NHCHO, —NO$_2$, —NHOH, —NHO-alkyl, —NHNH$_2$, substituted —NHNH$_2$, —CN, —CO$_2$H, —CO$_2$-alkyl, —CONH$_2$, —CONH-alkyl, —CON-(alkyl)$_2$, —CSNH$_2$, —CSNH-alkyl, —CSN-(alkyl)$_2$, —C(=NH)NH$_2$, —NHC(=NH)NH$_2$, —NHC(=NH)-alkyl, —SO-alkyl, —SO$_2$-alkyl, fluoroalkyl, —O-fluoroalkyl, —S-fluoroalkyl, —NHCO-(alkyl), —NHCO-(fluoroalkyl), —SO-(fluoroalkyl), —SO$_2$-(fluoroalkyl), —SH, —SO$_3$H, —SO$_2$NH$_2$, —SO$_2$—NH-alkyl, —SO$_2$N(alkyl)$_2$, alkenyl, alkynyl, aryl, or heterocycle;

Z represents O or S;

$R^4$ represents C=O, O, S, SO, SO$_2$, NH, N-alkyl, CH$_2$, CH-alkyl, CH-(aryl or heteroaryl), CHOH, CHO-alkyl, CHO-(aryl or heteroaryl), C-(alkyl)$_2$, C-(aryl or heteroaryl)$_2$, C-(alkyl)(aryl or heteroaryl), CHS-alkyl, CHS-(aryl or heteroaryl), C(OH)(alkyl), C(OH)(aryl or heteroaryl), C(OH)(cycloalkyl), N(OH), N-cycloalkyl, N-(aryl or heteroaryl), C-(cycloalkyl)$_2$, C-(aryl or heteroaryl)(cycloalkyl), C-(alkyl)(alkenyl), C-(alkyl)(alkynyl), C-(alkenyl)$_2$, C-(alkynyl)$_2$, C(alkynyl)(aryl or heteroaryl), C-(alkynyl)(alkenyl), C-(alkenyl)(aryl or heteroaryl), C-(cycloalkyl)(alkenyl), C-(cycloalkyl)(alkynyl), C-(aikyl)(aryl or heteroaryl), CH-(cycloalkyl), CH-(alkenyl), CH-(alkynyl), C-(alkyl)(cycloalkyl), C-(alkyl)(O-alkyl), C-(alkenyl)(O-alkyl), C-(alkynyl)(O-alkyl), C-(alkyl)(O-cycloalkyl), C-(alkenyl)(O-cycloalkyl), C-(alkynyl)(O-cycloalkyl), C-(aryl or heteroaryl)(O-alkyl), C-(aryl or heteroaryl)(O-cycloalkyl), C-(alkynyl)(S-alkyl), C-(alkynyl)(S-cycloalkyl), C-(alkenyl)(S-alkyl), C-(alkenyl)(S-cycloalkyl), C-(alkyl)(S-alkyl), C-(alkyl)(S-cycloalkyl), C-(aryl or heteroaryl)(S-alkyl), C-(aryl or heteroaryl)(S-cycloalkyl), N-(NH$_2$), N[NH(alkyl)], N[N(alkyl)$_2$], N[NH(cycloalkyl)], N[N(alkyl)(cycloalkyl)], CH(NH$_2$), CH[NH(alkyl)], CH[NH(cycloalkyl)], CH[N(alkyl)$_2$], CH[N(alkyl)(cycloalkyl)], CH[N(cycloalkyl)$_2$], C-(alkyl)(NH$_2$), C-(alkyl)[NH(alkyl)], C-(alkyl)[N(cycloalkyl)$_2$], C-(alkyl)[NH(cycloalkyl)], C-(alkyl)[N(alkyl)$_2$], C-(alkyl)[N(alkyl)(cycloalkyl)], C-(aryl or heteroaryl)(NH$_2$), C-(aryl or heteroaryl)[NH(alkyl)], C-(aryl or heteroaryl)[NH(cycloalkyl)], C-(aryl or heteroaryl)[N(alkyl)$_2$], or C-(aryl or heteroaryl)[N(alkyl)(cycloalkyl)]; and $R^5$ represents a substituted or unsubstituted heteroaryl or monocyclic aryl group;

at least one other compound which is an antitumor agent; and a pharmaceutically acceptable diluent or carrier.

2. A pharmaceutical composition, comprising:

an effective amount of a quinazoline compound according to formula I, or a pharmaceutically acceptable salt thereof, to inhibit growth and proliferation of cells of higher organisms and microorganisms, the compound according to formula I represented as follows:

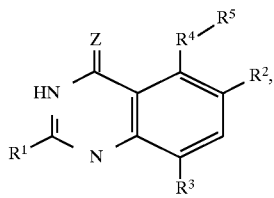

wherein:

- $R^1$ represents hydrogen, halogen, alkyl, —OH, —O-alkyl, —O-(aryl or heteroaryl), —S-alkyl, —S-(aryl or heteroaryl), —$NH_2$, —NH-alkyl, —N-(alkyl)$_2$, —NHCHO, —NHOH, —NHO-alkyl, —$NHNH_2$, substituted —$NHNH_2$, —NHC(=NH)$NH_2$, —NHC(=NH)alkyl, fluoroalkyl, cycloalkyl, alkenyl, alkynyl, aryl, or heterocycle;

- $R^2$ and R3, which may be the same or different, represent hydrogen, halogen, alkyl, cycloalkyl, —OH, —O-alkyl, —S-alkyl, —$NH_2$, —NH-alkyl, —N-(alkyl)$_2$, —NHCHO, —$NO_2$, —NHOH, —NHO-alkyl, —$NHNH_2$, substituted —$NHNH_2$, —CN, —$CO_2H$, —$CO_2$-alkyl, —$CONH_2$, —CONH-alkyl, —CON-(alkyl)$_2$, —$CSNH_2$, —CSNH-alkyl, —CSN-(alkyl)$_2$, —C(=NH)$NH_2$, —NHC(=NH)$NH_2$, —NHC(=NH)-alkyl, —SO-alkyl, —$SO_2$-alkyl, fluoroalkyl, —O-fluoroalkyl, —S-fluoroalkyl, —NHCO-(alkyl), —NHCO-(fluoroalkyl), —SO-(fluoroalkyl), —$SO_2$-(fluoroalkyl), —SH, —$SO_3H$, —$SO_2NH_2$, —$SO_2$-NH-alkyl, —$SO_2N$(alkyl)$_2$, alkenyl, alkynyl, aryl, or heterocycle;

- Z represents O or S;

- $R^4$ represents C=O, O, S, SO, $SO_2$, NH, N-alkyl, $CH_2$, CH-alkyl, CH-(anyl or heteroaryl), CHOH, CHO-alkyl, CHO-(aryl or heteroaryl), C-(alkyl)$_2$, C-(aryl or heteroaryl)$_2$, C-(alkyl)(aryl or heteroaryl), CHS-alkyl, CHS-(aryl or heteroaryl), C(OH)(alkyl), C(OH)(aryl or heteroaryl), C(OH)(cycloalkyl), N(OH), N-cycloalkyl, N-(aryl or heteroaryl), C-(cycloalkyl)$_2$, C-(aryl or heteroaryl)(cycloalkyl), C-(alkyl)(alkenyl), C-(alkyl)(alkynyl), C-(alkenyl)$_2$, C-(alkynyl)$_2$, C(alkynyl)(aryl or heteroaryl), C-(alkynyl)(alkenyl), C-(alkenyl)(aryl or heteroaryl), C-(cycloalkyl)(alkenyl), C-(cycloalkyl)(alkynyl), C-(alkyl)(aryl or heteroaryl), CH-(cycloalkyl), CH-(alkenyl), CH-(alkynyl), C-(alkyl)(cycloalkyl), C-(alkyl)(O-alkyl), C-(alkenyl)(O-alkyl), C-(alkynyl)(O-alkyl), C-(alkyl)(O-cycloalkyl), C-(alkenyl)(O-cycloalkyl), C-(alkynyl)(O-cycloalkyl), C-(aryl or heteroaryl)(O-alkyl), O-(aryl or heteroaryl)(O-cycloalkyl), C-(alkynyl)(S-alkyl), C-(alkynyl)(S-cycloalkyl), C-(alkenyl)(S-alkyl), C-(alkenyl)(S-cycloalkyl), C-(alkyl)(S-alkyl), C-(alkyl)(S-cycloalkyl), C-(aryl or heteroaryl)(S-alkyl), C-(aryl or heteroaryl)(S-cycloalkyl), N-($NH_2$), N[NH(alkyl)], N[N(alkyl)$_2$], N[NH(cycloalkyl)], N[N(alkyl)(cycloalkyl)], CH($NH_2$), CH[NH(alkyl)], CH[NH(cycloalkyl)], CH[N(alkyl)$_2$], CH[N(alkyl)(cycloalkyl)], CH[N(cycloalkyl)$_2$], C-(alkyl)($NH_2$), C-(alkyl)[NH(alkyl)], C-(alkyl)[N(cycloalkyl)$_2$], C-(alkyl)[NH(cycloalkyl)], C-(alkyl)[N(alkyl)$_2$], C-(alkyl)[N(alkyl)(cycloalkyl)], C-(aryl or heteroaryl)($NH_2$), C-(aryl or heteroaryl)[NH(alkyl)], C-(aryl or heteroaryl)[NH(cycloalkyl)], C-(aryl or heteroaryl)[N(alkyl)$_2$], or C-(aryl or heteroaryl)[N(alkyl)(cycloalkyl)]; and

- $R^5$ represents a substituted or unsubstituted heteroaryl or monocyclic aryl group;

at least one other agent which is an antibacterial agent, an antifungal agent, an antiparasitic agent, an antiviral agent, an antipsoriatic agent, an antiprotozoal agent, or an anticoccidial agent; and a pharmaceutically acceptable diluent or carrier.

3. A pharmaceutical composition according to claim 2, wherein said compound according to formula I is capable of inhibiting the enzyme thymidylate synthase.

4. A pharmaceutical composition according to claim 1, wherein said compound according to formula I is capable of inhibiting the enzyme thymidylate synthase.

5. A pharmaceutical composition according to claim 1, wherein said other compound is selected from the group consisting of mitotic inhibitors, alkylating agents, thymidylate synthase inhibitors, dihydrofolate reductase inhibitors, antimetabolites, intercalating antibiotics, enzymes, topoisomerase inhibitors or biological response modifiers.

6. A pharmaceutical composition according to claim 5, further comprising at least one other agent which is an antibacterial agent, an antifungal agent, an antiparasiatic agent, an antiviral agent, an antiparasiatic agent, an antiprotozoal agent or an anticoccidial agent.

* * * * *

UNITED STATES PATENT AND TRADEMARK OFFICE
CERTIFICATE OF CORRECTION

PATENT NO.: 5,885,996

DATED: March 23, 1999

INVENTOR(S): Stephen E. WEBBER et al.

Page 1 of 2

It is certified that an error appears in the above-identified patent and that said Letters Patent is hereby corrected as shown below:

Claim 1, col. 57, lines 57-64, delete the formula (I) " 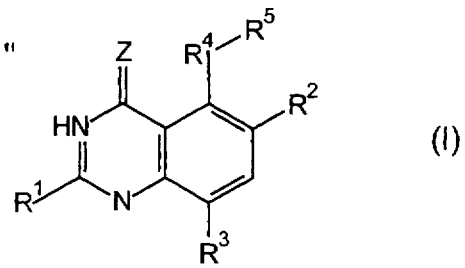 "

and insert therefor -- 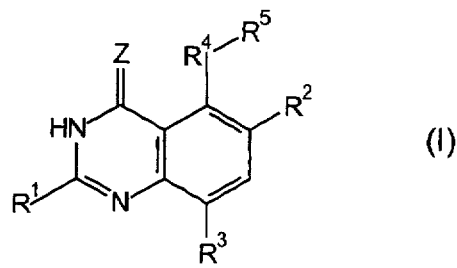 --

Claim 1, col. 58, line 34, "aikyl" should read --alkyl--.

UNITED STATES PATENT AND TRADEMARK OFFICE
CERTIFICATE OF CORRECTION

PATENT NO. : 5,885,996
DATED : March 23, 1999
INVENTOR(S) : Stephen E. WEBBER et al.

It is certified that error appears in the above-indentified patent and that said Letters Patent is hereby corrected as shown below:

Claim 2, col. 59, line 18, "R3" should read --$R^3$--;

line 34, "anyl" should read --aryl--.

Signed and Sealed this

Second Day of November, 1999

Attest:

Attesting Officer

Q. TODD DICKINSON

Acting Commissioner of Patents and Trademarks